US011173291B2

(12) United States Patent
Rairkar et al.

(10) Patent No.: US 11,173,291 B2
(45) Date of Patent: *Nov. 16, 2021

(54) IMPLANTABLE DRUG DELIVERY DEVICES FOR LOCALIZED DRUG DELIVERY

(71) Applicants: The Regents of the University of California, Oakland, CA (US); Alessa Therapeutics, Inc., San Francisco, CA (US)

(72) Inventors: Maithili Rairkar, San Francisco, CA (US); Pujan Desai, Oakland, CA (US); Carlos Schuler, San Francisco, CA (US); Maxime Daud, San Francisco, CA (US); Maxime D. Rappaport, San Francisco, CA (US); Pamela Munster, Hillsborough, CA (US); John Maroney, San Francisco, CA (US); Margaret McLaughlin, San Francisco, CA (US); Tobias H. Casab, San Francisco, CA (US); Keith Hall, San Francisco, CA (US); Scott Thomas, Oakland, CA (US)

(73) Assignees: The Regents of the University of California, Oakland, CA (US); Alessa Therapeutics, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/826,043

(22) Filed: Mar. 20, 2020

(65) Prior Publication Data

US 2021/0290920 A1    Sep. 23, 2021

(51) Int. Cl.
| A61M 31/00 | (2006.01) |
| A61K 9/00 | (2006.01) |
| A61K 31/277 | (2006.01) |
| A61B 10/02 | (2006.01) |
| A61B 17/34 | (2006.01) |

(52) U.S. Cl.
CPC ......... *A61M 31/002* (2013.01); *A61K 9/0024* (2013.01); *A61K 31/277* (2013.01); *A61M 31/007* (2013.01); *A61B 10/0241* (2013.01); *A61B 17/3468* (2013.01); *A61M 2205/04* (2013.01); *A61M 2210/166* (2013.01)

(58) Field of Classification Search
None
See application file for complete search history.

(56) References Cited

U.S. PATENT DOCUMENTS

| 3,279,996 A | 10/1966 | Long, Jr. et al. |
| 3,755,042 A | 8/1973 | Robertson et al. |
| 4,012,497 A * | 3/1977 | Schopflin ............ A61K 9/2036 424/432 |
| 4,144,317 A | 3/1979 | Higuchi et al. |
| 4,304,765 A | 12/1981 | Shell et al. |
| 4,482,053 A | 11/1984 | Alpern et al. |
| 4,668,506 A | 5/1987 | Bawa |
| 4,750,619 A | 6/1988 | Cohen et al. |
| 4,959,217 A | 9/1990 | Sanders et al. |
| 4,985,253 A * | 1/1991 | Fujioka ............... A61K 9/2036 424/422 |
| 5,733,565 A * | 3/1998 | Moo-Young ......... A61K 9/0092 424/424 |
| 5,824,074 A | 10/1998 | Koch |
| 6,071,305 A | 6/2000 | Brown et al. |
| 6,113,528 A | 9/2000 | Moran |
| 6,117,441 A | 9/2000 | Moo-Young et al. |
| 6,196,993 B1 | 3/2001 | Cohan et al. |
| 6,331,313 B1 | 12/2001 | Wong et al. |
| 6,358,276 B1 | 3/2002 | Edwin |
| 6,599,275 B1 * | 7/2003 | Fischer, Jr. ......... A61K 51/1282 424/422 |
| 6,623,519 B2 | 9/2003 | Edwin et al. |
| 6,881,220 B2 | 4/2005 | Edwin et al. |
| 7,658,727 B1 | 2/2010 | Fernandes et al. |
| 7,976,862 B2 | 7/2011 | Anderson et al. |
| 8,182,464 B2 | 5/2012 | Lee et al. |
| 8,795,711 B2 | 8/2014 | De Juan, Jr. et al. |

(Continued)

FOREIGN PATENT DOCUMENTS

| CN | 1583834 | 2/2005 |
| CN | 101437570 A | 5/2009 |

(Continued)

OTHER PUBLICATIONS

Paulsen "Advantages of Manufacturing Silicone Drug-Eluting Components via Ultraviolet Light Vulcanization Process" 2012 www.medicaldesignbriefs.com/component/content/article/mdb/features/applications/12817 5 pages (Year: 2012).*
Simtec "Properties of Liquid Silicone Rubber Part I" 2016 www.simtec-silicone.com/properties-of-liquid-silicone-rubber-part-1/ 7 pages (Year: 2016).*
Stone et al. Technology in Cancer Research and Treatment 2017 16(5):654-661 (Year: 2017).*
Tres et al. Molecular Pharmaceutics 2015 12:1512-1522 (Year: 2015).*
(Reference Y) Mitterberger et al. Cancer Imaging 2010 10:40-48 (Year: 2010).*
Silbione® Biomedical LSR (01 to 70 ShA) 4 pages (Year: 2015).*
www.silbione.com/frequently-asked-questions 3 pages (Year: 2018).*

(Continued)

*Primary Examiner* — Robert A Wax
*Assistant Examiner* — Caralynne E Helm
(74) *Attorney, Agent, or Firm* — Edward J. Baba; Bozicevic, Field & Francis LLP

(57) ABSTRACT

Provided herein are drug implants comprising a therapeutically active agent for the treatment of disease in a subject. In some cases, the drug implant may comprise a polymer matrix and a therapeutically active agent disposed therein. Additionally provided are methods for manufacturing the drug implants and methods of treating diseases with the implants. In some cases, the drug implant may comprise bicalutamide, e.g., for use in the treatment of prostate cancer.

16 Claims, 23 Drawing Sheets

(56) References Cited

U.S. PATENT DOCUMENTS

| | | |
|---|---|---|
| 8,801,694 B2 | 8/2014 | Lee et al. |
| 8,834,915 B2 | 9/2014 | Su et al. |
| 8,999,945 B2 | 4/2015 | Shemi |
| 9,005,649 B2 | 4/2015 | Ho et al. |
| 9,107,816 B2 | 8/2015 | Lee et al. |
| 9,345,867 B2 | 5/2016 | Browning |
| 9,561,353 B2 | 2/2017 | Lee et al. |
| 9,586,035 B2 | 3/2017 | Cima et al. |
| 10,532,132 B2 | 1/2020 | Tobias et al. |
| 2002/0049426 A1 | 4/2002 | Butler et al. |
| 2003/0147936 A1* | 8/2003 | Sahadevan .......... A61K 9/0024 424/426 |
| 2004/0067257 A1* | 4/2004 | Bateman ............... A61P 35/00 424/471 |
| 2004/0247674 A1* | 12/2004 | Haapakumpu ......... A61K 31/56 424/471 |
| 2005/0129728 A1* | 6/2005 | Martinod ................ A61P 7/06 424/423 |
| 2005/0177118 A1 | 8/2005 | Hoganson et al. |
| 2005/0187612 A1 | 8/2005 | Edwin |
| 2005/0268573 A1 | 12/2005 | Yan |
| 2006/0093639 A1 | 5/2006 | Starkebaum |
| 2007/0009564 A1* | 1/2007 | McClain .............. A61K 9/1694 424/423 |
| 2007/0088336 A1 | 4/2007 | Dalton |
| 2008/0245375 A1 | 10/2008 | Trudel |
| 2008/0286205 A1* | 11/2008 | Lennernas ............. A61P 35/00 424/9.3 |
| 2009/0104243 A1 | 4/2009 | Utkhede et al. |
| 2009/0149833 A1 | 6/2009 | Cima et al. |
| 2009/0149838 A1 | 6/2009 | Cassada |
| 2009/0311304 A1 | 12/2009 | Borck et al. |
| 2010/0003297 A1 | 1/2010 | Tobias et al. |
| 2010/0133133 A1 | 6/2010 | Hamas |
| 2011/0229457 A1 | 9/2011 | Kloke et al. |
| 2012/0083751 A1 | 4/2012 | Dalton |
| 2012/0130300 A1 | 5/2012 | Stavchansky et al. |
| 2012/0203203 A1 | 8/2012 | Lee et al. |
| 2012/0208755 A1 | 8/2012 | Leung |
| 2013/0325121 A1 | 12/2013 | Whatley et al. |
| 2014/0107088 A1* | 4/2014 | Wilsey ................... A61K 38/27 514/173 |
| 2015/0045687 A1 | 2/2015 | Nakai et al. |
| 2015/0080847 A1 | 3/2015 | Cima et al. |
| 2015/0182516 A1 | 7/2015 | Giesing |
| 2015/0208982 A1 | 7/2015 | Ho et al. |
| 2016/0038728 A1* | 2/2016 | Browning ............... A61F 6/142 604/60 |
| 2016/0051477 A1 | 2/2016 | Gopinathan |
| 2016/0243291 A1 | 8/2016 | Reich |
| 2016/0262923 A1* | 9/2016 | Ahola .................. A61K 31/567 |
| 2016/0310644 A1 | 10/2016 | Arps et al. |
| 2017/0157360 A1 | 6/2017 | Cima et al. |
| 2017/0224970 A1 | 8/2017 | Munster et al. |
| 2018/0042549 A1 | 2/2018 | Ho et al. |
| 2018/0140748 A1 | 5/2018 | Lee et al. |
| 2018/0333509 A1 | 11/2018 | Aston et al. |
| 2019/0184145 A1 | 6/2019 | Munster et al. |

FOREIGN PATENT DOCUMENTS

| | | | |
|---|---|---|---|
| CN | 101896221 A | 11/2010 | |
| CN | 102596174 A | 7/2012 | |
| CN | 103379902 A | 10/2013 | |
| CN | 103784244 A | 5/2014 | |
| CN | 103785101 A | 5/2014 | |
| CN | 107753418 A | 3/2018 | |
| EP | 2475354 A2 | 7/2012 | |
| GB | 2154138 A | 9/1985 | |
| JP | 2011505988 A | 3/2011 | |
| JP | 2013213020 A | 10/2013 | |
| JP | 2014509315 A | 4/2014 | |
| KR | 20130126266 A | 11/2013 | |
| WO | 9823228 A1 | 6/1998 | |
| WO | 0018327 A1 | 4/2000 | |
| WO | 0047232 A1 | 8/2000 | |
| WO | WO-0047232 A1 * | 8/2000 | .......... A61K 9/2036 |
| WO | 2005039537 A1 | 5/2005 | |
| WO | 2010065358 A1 | 6/2010 | |
| WO | 2012047931 A1 | 4/2012 | |
| WO | 2012048114 A1 | 4/2012 | |
| WO | 2012170578 A1 | 12/2012 | |
| WO | 2013148682 A1 | 10/2013 | |
| WO | 2014047221 A1 | 3/2014 | |
| WO | 2016028774 A1 | 2/2016 | |
| WO | 2016149561 A1 | 9/2016 | |

OTHER PUBLICATIONS

Geng et al. Journal of Applied Plymer Science 2017 45544:1-8 (Year: 2017).*
MED-4842 reference (Year: 2018).*
MED-4880 reference (Year: 2018).*
Reilly et al (2004) "Silicones as a Material of Choice for Drug Delivery Applications", 31st Annual Meeting and Exposition of the Controlled Release Society, 10 pages.
Reilly et al (2006) "Silicones for Drug-Delivery Applications", MDDI, 9 pages.
ClinicalTrials.gov: NCT04284761, A Study to Establish the feasibility of Biolen for the Local Delivery of Bicalutamide in Patients with Prostate Cancer (Biolen-PC).
EP15833347.6 Extended European Search Report dated Jan. 23, 2018.
EP19179965.9 Extended European Search Report dated Nov. 13, 2019.
Jakawich. A New Twist on Treating Chronic Bladder Pain. Pain Research Forum (website). Aug. 16, 2012. 4 pages. Retrieved Jul. 31, 2019 at URL: <https://www.painresearchforum.org/news/19233-new-twist-treating-chronic-bladder-pain>.
PCT/US2015/045687 International Search Report and Written Opinion dated Nov. 24, 2015.
U.S. Appl. No. 15/502,742 Office Action dated Aug. 15, 2019.
U.S. Appl. No. 16/273,760 Office Action dated May 28, 2019.
U.S. Appl. No. 15/502,742 Office Action dated Feb. 27, 2020.
U.S. Appl. No. 16/273,760 Office Action dated Dec. 4, 2019.
U.S. Appl. No. 16/826,022.
U.S. Appl. No. 16/826,064.
Bassetto et al 2016 European Journal of Medicinal Chemistry, 118: 230-243.
Fung et al 1997 Advanced Drug Delivery Reviews, 26: 209-230.
Karami et al 2014 International Journal of Pharmaceutics, 460: 158-164.
Mitterberger et al 2010 Cancer Imaging, 10:40-48.
Sabel et al 1990 Journal of Pharmacology and Experimental Therapeutics, 255(2):914-922.
Simtec 2016 Properties of Liquid Silicone Rubber Part I, www.simtec-silicone.com/properties-of-liquid-silicone-rubber-part-1/7.
Cockshott, et al. 2004, "Clinical Pharmacokinetics and Metabolism" 43(13): 855-878.
Silbione® Biomedical LSR (2015) (01 to 70 ShA), pp. 1-4.
www.silbione.com/frequently-asked-questions (2014) 3 pages.
Casodex® (2017)reference (www.accessdata.fda.gov/drugsatfda_docs/label/2017/020498s028lbl.pdf.
PubChem Gestodene record (2012) (pubchem.ncbi.nlm.nih.gov/source/hsdb/3594#section=Human-Toxicity-Excerpts-(Complete).
MED-4810 (2018) reference 2 pages.
MED-4830 (2018) reference 2 pages.
Elastosil LR 3003/40 reference (2012).
Mashak et al., Radiation Physics and Chemistry 75:229-235 (2006).
Tsoi thesis "Formulation Development of a Polymer-Drug Matrix with a Controlled Release Profile for the Treatment of Glaucoma" (2013).
MED-4842 reference (2018).
MED-4880 reference (2018).

* cited by examiner

IMPLANTABLE DRUG DELIVERY DEVICES FOR LOCALIZED DRUG DELIVERY

BACKGROUND OF THE DISCLOSURE

The burden of suffering from prostate cancer in the United States is significant. In 2009, approximately 192,000 men were diagnosed with prostate cancer, and 27,000 men were expected to die from this disease. Approximately 2.2 million living American men have been diagnosed with prostate cancer, and some are living with metastatic disease, a painful and functionally limiting stage of the disease. Prostate cancer is by far the most commonly diagnosed cancer among American men and remains the second leading cause of cancer death in men. Hormonal therapy of prostate cancer includes a wide variety of treatments designed to affect cells whose normal functioning depends on androgens, which include testosterone and dihydrotestosterone, among others. Prostate cancer cells are generally very susceptible to treatments that lower androgen levels or affect the normal action of these hormones.

Bicalutamide is an anti-androgen that can be used to treat prostate cancer. Bicalutamide is a member of the nonsteroidal antiandrogen group of medications and works by blocking the androgen receptor. Bicalutamide has been associated with a number of side effects, which may be due, in part, to the relatively high amounts of bicalutamide that are administered systemically to obtain a therapeutic benefit. Thus, local administration of smaller amounts of bicalutamide may be able to achieve a therapeutic benefit, and prevent or reduce side effects or toxicity of systemic bicalutamide administration.

SUMMARY OF THE DISCLOSURE

A need exists for improved drug implants that can be used to deliver a therapeutically active agent (e.g., bicalutamide) directly to a target tissue of a subject. Provided herein are drug implants that can deliver a therapeutically effective amount of a drug directly to a target tissue. Further provided herein are drug implants that, when implanted into a target tissue, result in a high concentration of drug within the target tissue, and a low concentration of drug in the systemic circulation (e.g., in the blood plasma). In some cases, the ability of the drug implants provided herein to deliver a therapeutically effective amount of the drug directly to the target tissue, while achieving low concentrations of the drug in the systemic circulation, may reduce or eliminate toxicity of the drug that would otherwise occur from systemic administration. In addition, delivery of the drug directly to the target tissue by way of the drug implants described herein, ensures that the target tissue receives a therapeutically effective amount of drug. In further aspects, the drug implants provided herein are capable of being loaded with a large amount of drug such that the drug implant is capable of sustained release of the drug to the target tissue for extended periods of time.

In one aspect, an implant is provided comprising bicalutamide dispersed in a polymer matrix, resulting in sustained release of the bicalutamide at a rate of at least 0.1 µg/day for least 6 months after implantation of the implant in a prostate tissue or a tissue near a prostate. In some cases, the bicalutamide is in solid form. In some cases, a volume of the implant is at least 10 mm³. In some cases, a length of the implant is at least 1 mm. In some cases, a length of the implant is at least 3 mm. In some cases, a diameter of the implant is at least 0.1 mm. In some cases, a diameter of the implant is at least 0.8 mm. In some cases, the implant lacks at least one of a sheath, a scaffold, a retention member for retaining the implant within a target tissue, or a combination thereof. In some cases, the implant comprises the bicalutamide in an amount of at least 30% w/w. In some cases, a total dose of the bicalutamide per implant is at least 1 mg. In some cases, the polymer matrix comprises silicone. In some cases, the silicone has a Shore A hardness of at least 30 durometer. In some cases, the bicalutamide has a median particle size of less than 10 microns. In some cases, the bicalutamide has a D90 of less than 15 microns. In some cases, the cumulative release of the bicalutamide in an in vitro model is at least one of the following: at least 100 µg on day 1, at least 1,500 µg on day 50, or at least 2,000 µg on day 100. In some cases, the implant is configured for delivery to the prostate tissue or the tissue near the prostate through a lumen of a needle or a catheter. In some cases, the implant consists essentially of the polymer matrix and the bicalutamide dispersed in the polymer matrix.

In another aspect, a method of treating a subject in need thereof is provided, the method comprising delivering an implant of any one of the preceding to the prostate tissue or the tissue near the prostate of the subject, thereby treating the subject. In some cases, the subject has a proliferative disease of the prostate. In some cases, the proliferative disease of the prostate is prostate cancer or benign prostatic hyperplasia.

In another aspect, a prostate implant is provided comprising: a polymer matrix; and bicalutamide dispersed in the polymer matrix at an amount of at least 30% w/w. In some cases, the prostate implant releases at least 0.1 µg/day of the bicalutamide at 6 months after implantation in a subject. In some cases, the bicalutamide is in solid form. In some cases, the solid form has a median particle size of less than 10 microns. In some cases, the solid form has a D90 of less than 15 microns. In some cases, the prostate implant has a Shore A hardness of at least 30 durometer. In some cases, the polymer matrix is a silicone. In some cases, the silicone has one or more of the following properties a Shore A hardness of at least 30 durometer and a curing temperature less than a melting point of bicalutamide. In some cases, at least 50% of the bicalutamide remains in the polymer matrix after 100 days of implantation. In some cases, the polymer matrix inhibits modulation of the bicalutamide in the prostate implant. In some cases, the modulation comprises degradation. In some cases, the degradation is determined by measuring an amount of the bicalutamide in an eluent after incubating the prostate implant containing the bicalutamide in a solution comprising 1% SDS containing 0.05 N NaOH for 8 hours at 37° C. In some cases, a volume of the prostate implant is at least 10 mm³. In some cases, a length of the prostate implant is from 1 mm to 30 mm. In some cases, a length of the prostate implant is from 5 mm to 25 mm. In some cases, a diameter of the prostate implant is from 0.1 mm to 1.5 mm. In some cases, the bicalutamide is dispersed in the polymer matrix at an amount of at least 40% w/w. In some cases, at least 50% of an outer surface of the prostate implant is configured to directly contact a prostate tissue or a tissue near a prostate. In some cases, the prostate implant is deliverable using a cannula of a prostate biopsy needle or a Mick® needle. In some cases, the prostate implant consists essentially of the polymer matrix and the bicalutamide dispersed in the polymer matrix.

In another aspect, a method of treating a proliferative disease of the prostate of a subject is provided, the method comprising implanting one or more implants into a prostate tissue or a tissue near a prostate, wherein each of the one or more implants comprises a polymer matrix and bicalutamide, and wherein the one or more implants provides a therapeutically effective amount of the bicalutamide to the prostate for at least 6 months. In some cases, the proliferative disease of the prostate is prostate cancer or benign prostatic hyperplasia. In some cases, the bicalutamide is dispersed within the polymer matrix, prior to the implanting. In some cases, the implanting comprises deploying each implant of the one or more implants to the prostate tissue or the tissue near the prostate through a lumen of a needle or a catheter. In some cases, the needle is a Mick® needle. In some cases, the implanting occurs via transperineal administration. In some cases, the transperineal administration comprises using a template guided needle. In some cases, the polymer matrix inhibits degradation of the bicalutamide. In some cases, the degradation is determined by measuring an amount of the bicalutamide in an eluent after incubating an implant of the one or more implants in a solution comprising 1% SDS containing 0.05 NaOH for 8 hours at 37° C. In some cases, the polymer matrix is substantially non-biodegradable. In some cases, the polymer matrix comprises silicone. In some cases, a total dose of the bicalutamide administered to the subject is less than a total dose of bicalutamide when administered to a subject by oral administration. In some cases, the total dose of the bicalutamide administered to the subject is less than 100 mg over a period of 6 months. In some cases, the implanting results in a blood plasma concentration of bicalutamide that is less than a blood plasma concentration of bicalutamide obtained when bicalutamide is administered to a subject by oral administration, and wherein the implanting results in a steady state blood plasma concentration of (R)-bicalutamide that is less than 5 µg/mL. In some cases, the implanting comprises transperineal implantation of at least three implants. In some cases, each of the one or more implants has a volume of at least 10 mm³.

In another aspect, a method of treating a proliferative disease of the prostate of a subject is provided, the method comprising implanting one or more implants into a prostate tissue or a tissue near a prostate, wherein each of the one or more implants comprises a polymer matrix and bicalutamide, and wherein the implanting results in a steady state blood plasma concentration of (R)-bicalutamide that is less than 5 µg/mL. In some cases, the implanting comprises deploying each implant of the one or more implants to the prostate tissue or the tissue near the prostate through a lumen of a needle or a catheter. In some cases, a total dose of the bicalutamide administered to the subject is less than a total dose of bicalutamide when administered to a subject by oral administration. In some cases, the total dose of the bicalutamide administered to the subject is less than 100 mg over a period of 6 months.

In one aspect, an implant is provided comprising a biocompatible, substantially non-biodegradable polymer matrix; and an anti-androgen dispersed throughout the polymer matrix. In another aspect, an implant is provided comprising a biocompatible polymer matrix; and a therapeutically active agent dispersed throughout the polymer matrix, wherein the implant delivers a therapeutically effective amount of the therapeutically active agent to a target tissue of a subject for at least 24 months when the implant is disposed in the target tissue of the subject. In another aspect, an implant is provided comprising a biocompatible, substantially non-biodegradable polymer matrix; and an anti-androgen in crystalline form. In yet another aspect, an implant is provided comprising a biocompatible, substantially non-biodegradable polymer matrix; and an anti-androgen dispersed throughout the polymer matrix at an amount from 10 to 70% w/w.

In some cases, the implant, when disposed in the target tissue of the subject, releases at least 0.1 µg/day of the therapeutically active agent or the anti-androgen at 24 months after implantation. In some cases, the therapeutically active agent or the anti-androgen has a median particle size of less than 10 microns. In some cases, the implant has a Shore A hardness of at least 30 durometer when loaded with 60% w/w of a therapeutically active agent. In some cases, at least 99% of the polymer matrix remains in the target tissue of the subject after implantation for at least 600 days. In some cases, the implant is visible by ultrasound when disposed in the target tissue of the subject. In some cases, the therapeutically active agent or the anti-androgen has a melting temperature that is greater than a curing temperature of the polymer matrix. In some cases, the melting temperature is greater than 150° C. In some cases, the polymer matrix inhibits degradation of the therapeutically active agent or the anti-androgen in the implant. In some cases, the polymer matrix inhibits degradation of the therapeutically active agent or the anti-androgen by an esterase or an amidase. In some cases, the degradation is determined by measuring the amount of the therapeutically active agent or the anti-androgen in an eluent after incubating the implant containing the therapeutically active agent or the anti-androgen in a solution comprising 1% SDS containing 0.05 N NaOH for 8 hours at 37° C. In some cases, the implant is elongate. In some cases, the implant is cylindrical. In some cases, the implant is tubular. In some cases, a diameter of the implant is less than 1 mm. In some cases, a diameter of the implant is from 0.5 mm to 1.5 mm. In some cases, a diameter of the implant is from 0.7 mm to 1.3 mm. In some cases, a diameter of the implant is from 0.9 mm to 1.1 mm. In some cases, a diameter of the implant is about 1 mm. In some cases, a length of the implant is less than 20 mm. In some cases, a length of the implant is from 5 mm to 25 mm. In some cases, a length of the implant is from 10 mm to 20 mm. In some cases, a length of the implant is from 12 mm to 18 mm. In some cases, a length of the implant is about 15 mm. In some cases, the implant further comprises a coating. In some cases, the coating partially covers the implant. In some cases, the coating substantially covers the implant. In some cases, the coating covers the implant. In some cases, the therapeutically active agent is an anti-androgen. In some cases, the therapeutically active agent or the anti-androgen is bicalutamide. In some cases, the implant is sterile. In some cases, the implant is disposed in a sterilized package. In some cases, the polymer matrix is at least 95% cured, at least 96% cured, at least 97% cured, at least 98% cured, at least 99% cured, or at least 99.9% cured. In some cases, the polymer matrix comprises silicone. In some cases, the silicone is Silbione® LSR D370 as manufactured by Elkem. In some cases, the silicone is DDU 4870 as manufactured by NuSil™ (Trelyst). In some cases, the implant is configured to be implanted into prostate tissue of a subject. In some cases, the implant lacks a metal.

In another aspect, a method of manufacturing an implant suitable for implantation into the prostate of a subject is provided, the method comprising: (a) mixing an amount of uncured biocompatible, substantially non-biodegradable polymer with an amount of anti-androgen to form a mixture; (b) molding the mixture to create a molded mixture; and (c) curing the molded mixture by heating the molded mixture for a period of time. In some cases, the amount of anti-androgen is between 10% w/w and 70% w/w of the uncured biocompatible, substantially non-biodegradable polymer. In some cases, the anti-androgen is bicalutamide. In some cases, the biocompatible, substantially non-biodegradable polymer is a silicone. In some cases, the silicone is Silbione® LSR D370 as manufactured by Elkem. In some cases, the silicone is DDU 4870 as manufactured by NuSil™ (Trelyst). In some cases, the curing of (c) further comprises heating the molded mixture at a temperature from about 150° C. to about 200° C. for 3 to 8 minutes. In some cases, the mixture further comprises a solvent. In some cases, the solvent is selected from the group consisting of: pentane, dichloromethane, tetrahydrofuran, heptane, toluene, and hexane. In some cases, the mixture is molded by a transfer molding process. In some cases, the method further comprises performing an analysis on the implant. In some cases, the analysis is selected from the group consisting of: differential scanning calorimetry (DSC), deployment of implant in surrogate tissue, elution testing, viscometry, high pressure liquid chromatography (HPLC), and simulated in vivo stability assay.

In another aspect, a kit is provided comprising: a sterilized package comprising an implant according to any one of the preceding; and instructions for implanting the implant into a target tissue of a subject. In some cases, the implant is configured for delivery into a human prostate, tissue adjacent the human prostate, or both. In some cases, the sterilized package is formed from a foil. In some cases, the kit further comprises one or more surgical tools for implanting the implant into the target tissue of the subject. In some cases, the one or more surgical tools comprises a needle, forceps, a trocar, or a stylet.

In another aspect, a method of treating a disease in a subject in need thereof is provided, comprising: implanting an implant of any one of the preceding into the prostate of the subject, thereby treating the disease. In another aspect, a method of treating a disease in a subject in need thereof is provided, comprising: implanting a substantially non-biodegradable implant comprising a biocompatible polymer matrix and an anti-androgen drug dispersed throughout the biocompatible polymer matrix into the prostate of the subject, thereby treating the disease.

In some cases, the prostate comprises prostate tissue, tissue adjacent the prostate tissue, or both. In some cases, the disease is a proliferative disease or disorder of the prostate (e.g., prostate cancer, benign prostatic hyperplasia). In some cases, the method further comprises disposing a distal end of an elongate tube in the subject's prostate or tissue adjacent the prostate. In some cases, a portion of the elongate tube is disposed through a first portion of a grid such that a first position of the elongate tube in the subject is determined. In some cases, the elongate tube is a needle or a catheter. In some cases, a trocar is disposed within a lumen of the elongate tube. In some cases, the method further comprises removing the trocar from the lumen of the elongate tube. In some cases, the method further comprises after removing the trocar from the lumen of the elongate tube, positioning the implant within the lumen of the elongate tube. In some cases, the method further comprises pushing a stylet through the lumen of the elongate tube, thereby displacing the implant to the distal end of the elongate tube. In some cases, the method further comprises displacing the elongate tube away from the subject such the implant remains within the subject. In some cases, the stylet is disposed in a portion of the lumen of the elongate tube, a distal end of the stylet adjacent the implant such that the implant remains within the subject. In some cases, a portion of a second elongate tube is disposed through a second portion of the grid such that a position of the second elongate tube in the subject is determined.

BRIEF DESCRIPTION OF THE DRAWINGS

Various aspect of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
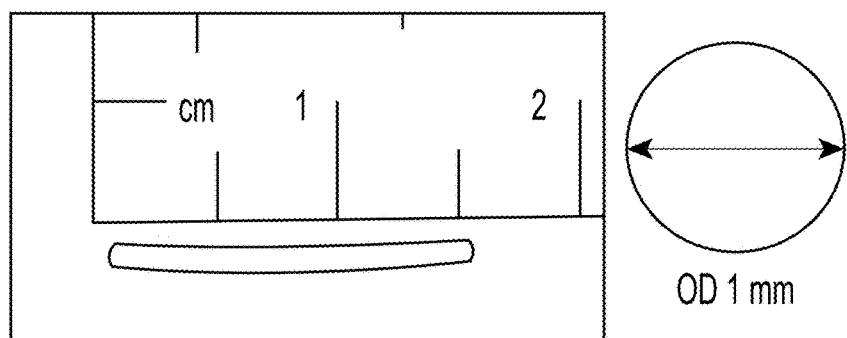
FIG. 1 depicts a non-limiting example of a molded implant according to aspects of the disclosure.
Figure 2A:
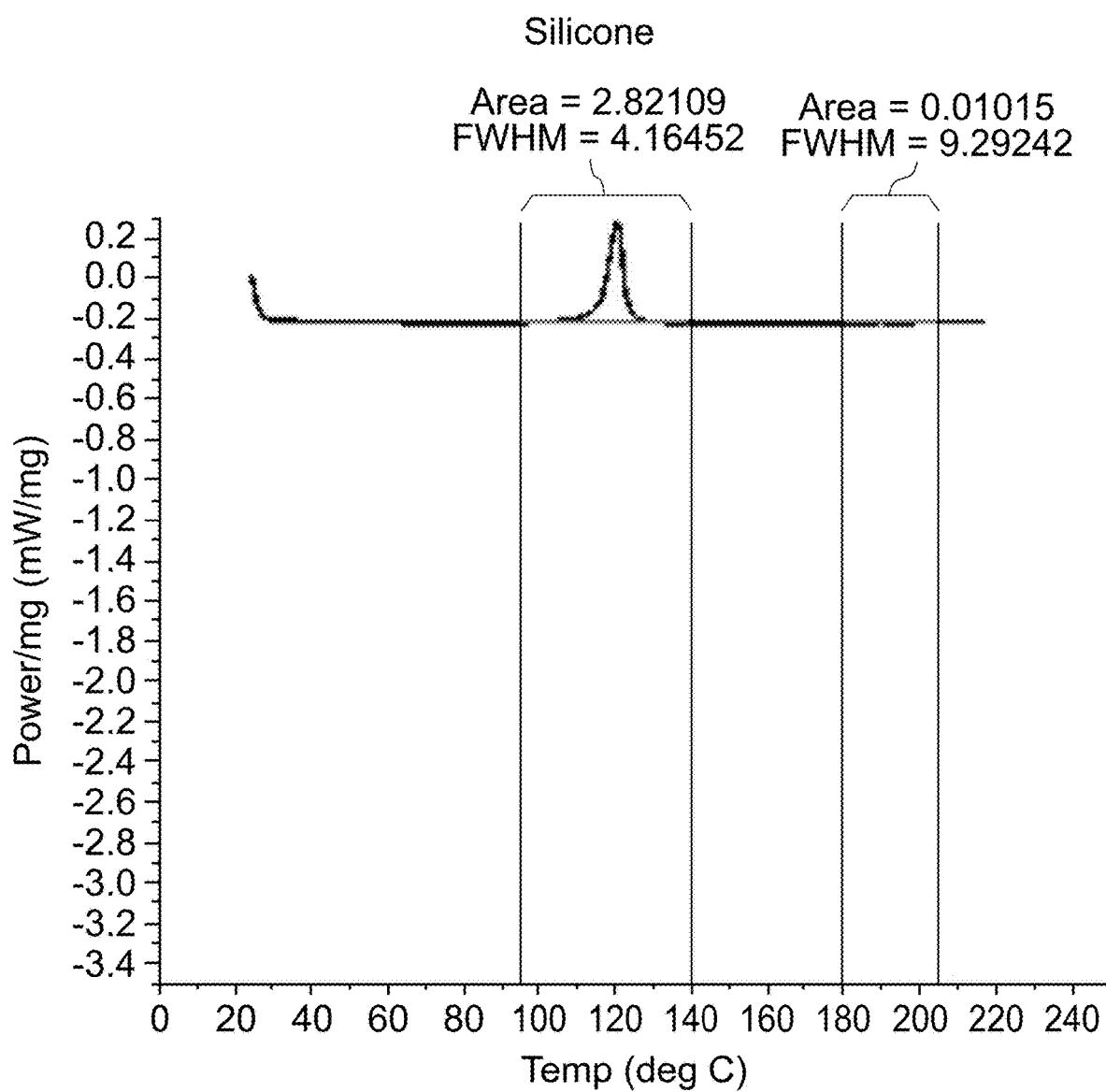
FIG. 2A, FIG. 2B, FIG. 2C, FIG. 2D, FIG. 2E, and FIG. 2F depict non-limiting examples of differential scanning calorimetry (DSC) thermograms of formulation components and molded rods according to aspects of the disclosure.
Figure 2B:
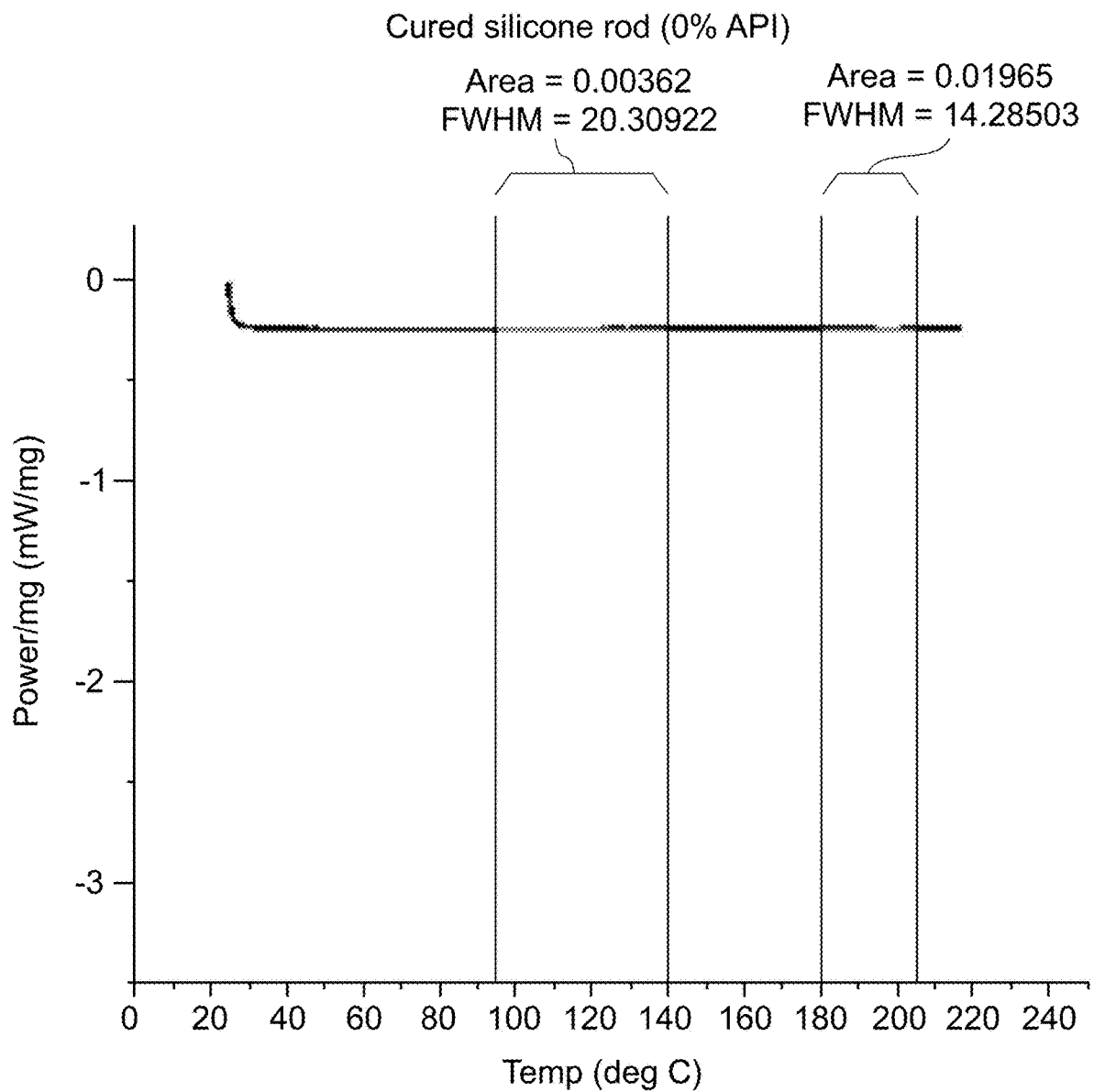
Figure 2C:
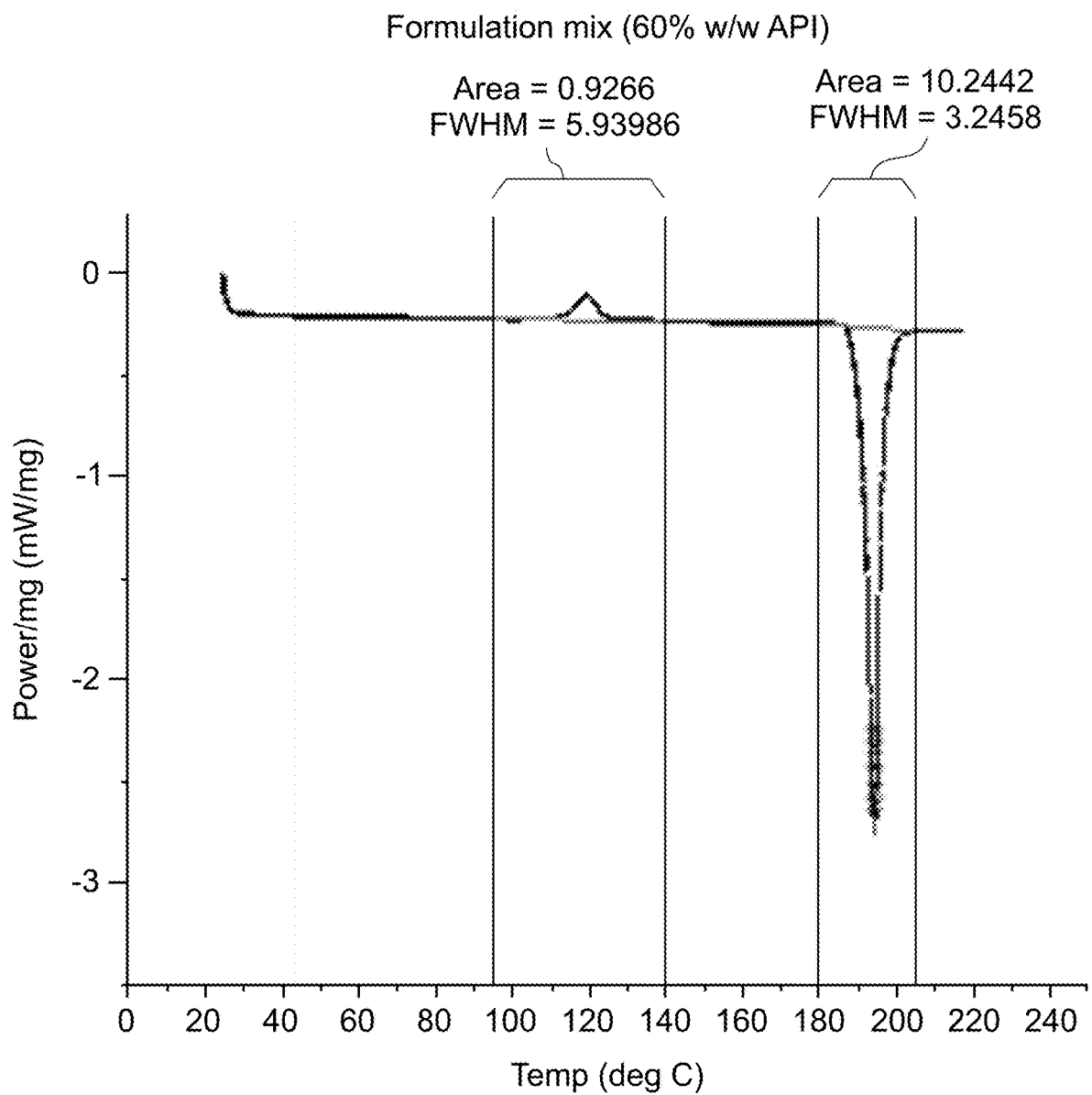
Figure 2D:
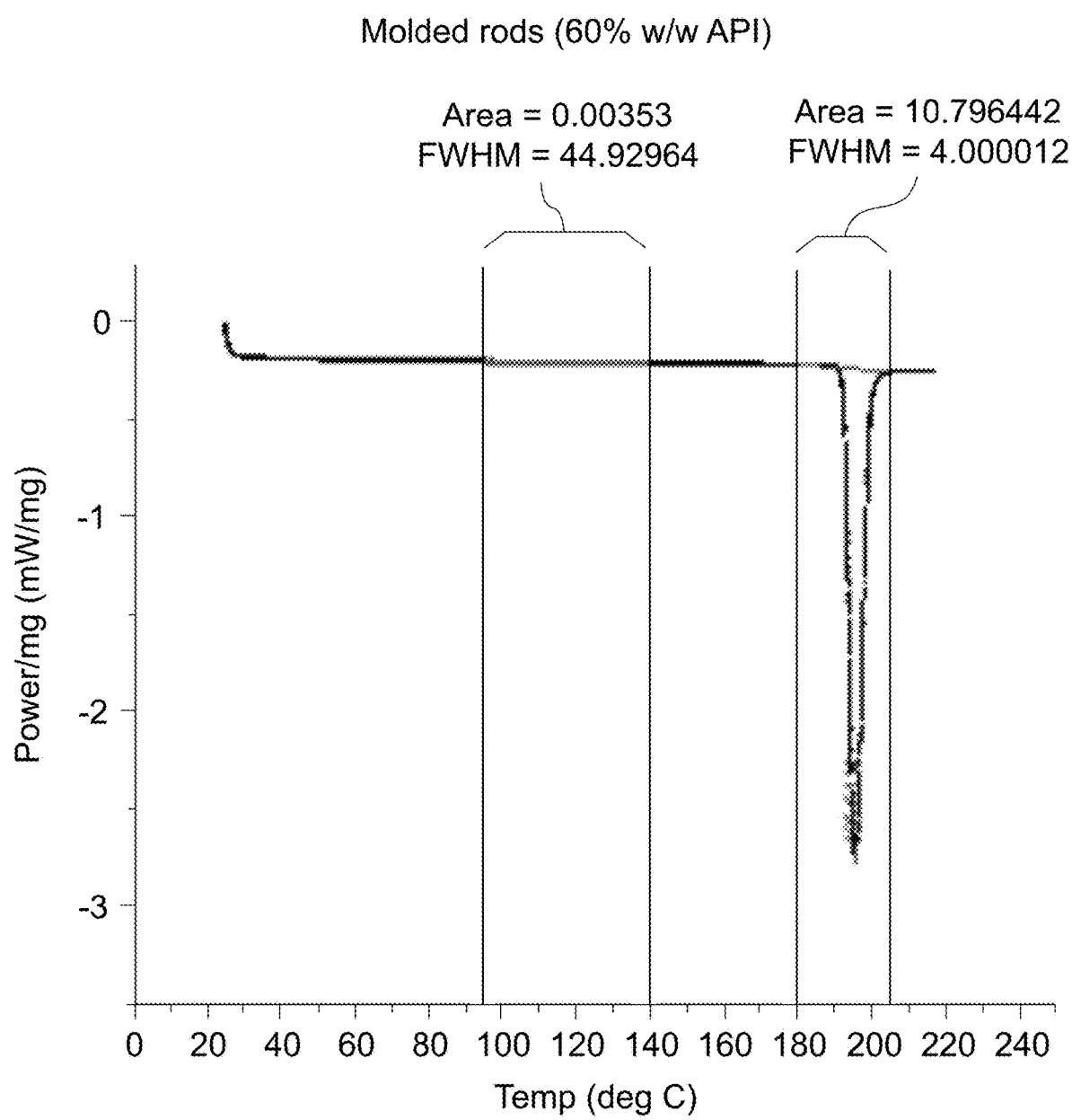
Figure 2E:
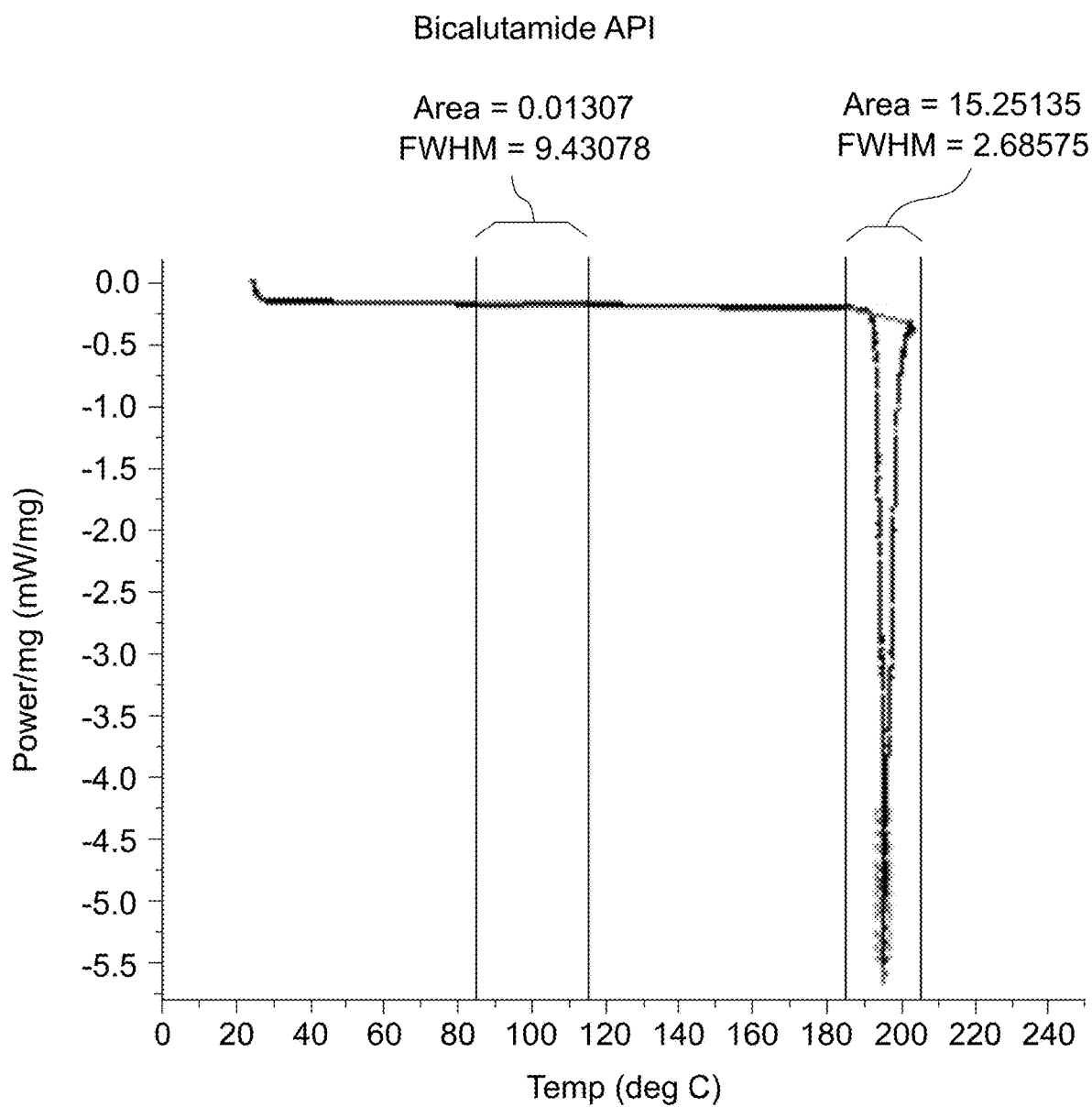
Figure 2F:
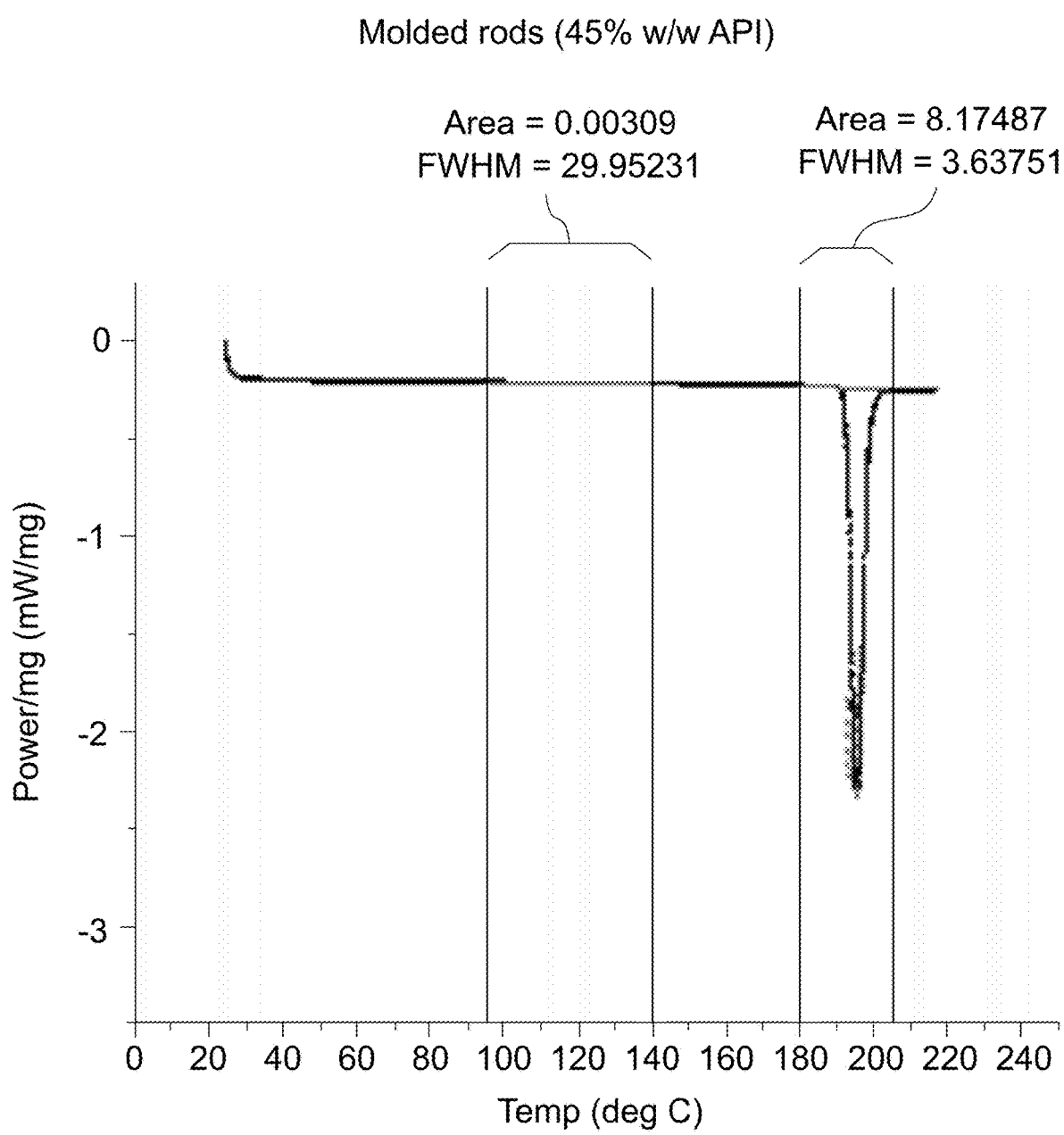

Provided herein are drug implants that are capable of delivering a therapeutically effective amount of a drug directly to a target tissue. Further provided herein are drug implants that, when implanted into a target tissue, result in a high concentration of drug within the target tissue, and a low concentration of drug in the systemic circulation (e.g., in the blood plasma). In some cases, the ability of the drug implants provided herein to deliver a therapeutically effective amount of the drug directly to the target tissue, while achieving low concentrations of the drug in the systemic circulation, may reduce or eliminate side effects or toxicity of the drug that would otherwise occur from systemic administration. In addition, delivery of the drug directly to the target tissue by way of the drug implants described herein, ensures that the target tissue receives a therapeutically effective amount of drug. In further aspects, the drug implants provided herein are capable of being loaded with a large amount of drug such that the drug implant is capable of sustained release of the drug to the target tissue for extended periods of time. In some aspects, the therapeutically active agent may be dispersed within a polymer matrix of the implant which may provide particular advantages (e.g., faster elution times, higher drug loading within the implant, etc.). In particular aspects, the drug implants provided herein may contain bicalutamide at high concentrations such that a therapeutically effective amount of bicalutamide can be administered directly to prostate tissue for long periods of time (6 months or greater) while maintaining low systemic concentrations of bicalutamide.

In various aspects, the drug implants disclosed herein may comprise a polymer matrix and a therapeutically active agent. In particular cases, the therapeutically active agent may be dispersed within the polymer matrix. The drug implants may be implanted into a target tissue, and may release a quantity of the therapeutically active agent over time. The therapeutically active agent may be a drug or active pharmaceutical ingredient (API) that may be effective to treat a disease or a symptom thereof. In some cases, the therapeutically active agent is bicalutamide, and the disease is a proliferative disease of the prostate (e.g., prostate cancer, benign prostatic hyperplasia). Further provided herein are methods of treating a disease by delivering a drug implant of the disclosure to a target tissue of a subject in need thereof in order to deliver a therapeutically effective amount of drug for extended periods of time. Additionally, methods of manufacturing drug implants and kits including drug implants are provided.

Drug Implants

Provided herein are drug implants (also referred to herein as "implants") suitable for delivering a therapeutically active agent to a target tissue. In some aspects of the disclosure, the implant comprises a polymer matrix and a therapeutically active agent dispersed therein. The therapeutically active agent or drug may be bicalutamide. The implants may be suitable for treating a proliferative disease of the prostate (e.g., prostate cancer, benign prostatic hyperplasia).

The polymer matrix may comprise any polymer material. Generally, the polymer material may be biocompatible. The term "biocompatible" as used herein refers to a property of a material that allows for prolonged contact with a tissue in a subject without causing toxicity or significant damage.

In some aspects, the polymer material may be "non-biodegradable" or "substantially non-biodegradable". The terms "non-biodegradable" or "substantially non-biodegradable", when used in reference to an implant of the disclosure, generally refer to an implant that is incapable or substantially incapable of being decomposed by microorganisms over the intended life of the implant. For example, a substantially non-biodegradable implant of the disclosure may have at least 99% of the polymer material remaining two years after implanting the device into a target tissue.

In certain aspects of the disclosure, the polymer matrix may comprise polysiloxane (silicone). The silicone may be any biocompatible silicone. In some cases, the silicone may be a medical grade silicone. In some cases, the silicone may be a United States Pharmacopeia (USP) Class V or USP Class VI certified silicone. In various aspects, the silicone may be any liquid silicone rubber (LSR). In some cases, the silicone may be a Silbione® Liquid Silicone Rubber (LSR) as manufactured by Elkem. In some cases, the Silbione® LSR may be one or more of Silbione® LSR 4301, Silbione® LSR 4305, Silbione® LSR 4310, Silbione® LSR 4325, Silbione® LSR 4330, Silbione® LSR 4340, Silbione® LSR 4350, Silbione® LSR 60, Silbione® LSR 4360, Silbione® LSR 4370, Silbione® LSR 4745, Silbione® LSR 4755, Silbione® LSR 4765, Silbione® LSR 4125, Silbione® LSR 4130, Silbione® LSR 4140, Silbione® LSR M301, Silbione® LSR M305, Silbione® LSR M310, Silbione® LSR M325, Silbione® LSR M330, Silbione® LSR M340, Silbione® LSR M350, Silbione® LSR M360, Silbione® LSR M365, Silbione® LSR M370, Silbione® LSR M125, Silbione® LSR M130, Silbione® LSR M140. In various aspects, the silicone may be Silbione® LSR D370. In some cases, the silicone may be a silicone manufactured by NuSil™ (Trelyst). In various aspects, the silicone may be DDU 4870 as manufactured by NuSil™ (Trelyst). In some cases, the silicone may be one or more of the following silicones as manufactured by NuSil™ (Trelyst): MED-4801, MED-4805, MED-4810, MED-5820, MED-5830, MED-5840, MED-5850, MED-5860, MED-5870, MED-4880, MED50-5338, MED-5440, MED-4842, and MED1-4855.

Additional non-biodegradable polymers which may be used herein include, without limitation, a silicone material, acrylates, polyethylenes, polyurethane, hydrogel, polyester, polypropylene, polytetrafluoroethylene (PTFE), expanded PTFE (ePTFE), polyether ether ketone (PEEK), nylon, extruded collagen, polymer foam, silicone rubber, polyethylene terephthalate, ultra-high molecular weight polyethylene, polycarbonate urethane, polyurethane, and polyimides.

The Shore A hardness scale measures the hardness of rubbers. A higher number on the scale refers to a firmer material, whereas a lower number on the scale refers to a softer material. Generally, the polymer material in the drug implant has a Shore A hardness of at least 30-durometer. For example, the polymer material may have a Shore A hardness of at least 30-durometer, at least 40-durometer, at least 50-durometer, at least 60-durometer, or at least 70-durometer. In one aspect, the uncured polymer material may have a Shore A hardness of 30-durometer, and the cured polymer material may have a Shore A hardness of 70-durometer.

The implant may further comprise a therapeutically active agent (also referred to herein as a "drug"). In particular aspects, the therapeutically active agent is bicalutamide. In some cases, the therapeutically active agent may be dispersed or distributed within the polymer matrix. In some cases, the therapeutically active agent may be dispersed or distributed throughout the polymer matrix. In some cases, the therapeutically active agent may be uniformly or homogeneously dispersed or distributed within the polymer matrix. In other cases, the therapeutically active agent may be heterogeneously dispersed or distributed within the polymer matrix. In other cases, the therapeutically active agent may be dispersed or distributed within the polymer matrix in a gradient. In particular aspects, the therapeutically active agent may be dispersed or distributed within the polymer matrix at the time of manufacture of the implant (e.g., the therapeutically active agent may be mixed with the polymer material prior to curing of the polymer material as disclosed herein). In some cases, providing the drug dispersed within the polymer matrix may be advantageous over other drug implants (e.g., those in which the drug is encapsulated in a capsule, or in the lumen of a tube). For example, having the drug dispersed within the polymer matrix may allow for higher loading of drug in the implant, faster elution rates, and the like.

In various aspects of the disclosure, the implant may comprise a therapeutically active agent (e.g., bicalutamide) in an amount from about 10% w/w to about 70% w/w. For example, the implant may comprise a therapeutically active agent (e.g., bicalutamide) in an amount of about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, or about 70% w/w. In various aspects, the implant may comprise a therapeutically active agent (e.g., bicalutamide) in an amount of at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, or at least about 70% w/w. In particular aspects, the therapeutically active agent is bicalutamide and is present in the implant in an amount of about 10% w/w, about 30% w/w, about 45% w/w, or about 60% w/w. In some cases, the disclosure provides drug implants loaded with high concentrations of bicalutamide (e.g., 60% w/w). In some cases, the implant may contain bicalutamide in an amount of at least 30% w/w. In some cases, the implant may contain bicalutamide in an amount of at least 40% w/w.

In various aspects of the disclosure, the implant may comprise a therapeutically active agent (e.g., bicalutamide) in an amount from about 5% volume/volume (v/v) to about 60% v/v. For example, the implant may comprise a therapeutically active agent (e.g., bicalutamide) in an amount of about 5% v/v, about 10% v/v, about 15% v/v, about 20% v/v, about 25% v/v, about 30% v/v, about 35% v/v, about 40% v/v, about 45% v/v, about 50% v/v, about 55% v/v, or about 60% v/v. In various aspects, the implant may comprise a therapeutically active agent (e.g., bicalutamide) in an amount of at least about 5% v/v, at least about 10% v/v, at least about 15% v/v, at least about 20% v/v, at least about 25% v/v, at least about 30% v/v, at least about 35% v/v, at least about 40% v/v, at least about 45% v/v, at least about 50% v/v, at least about 55% v/v, or at least about 60% v/v. In particular aspects, the therapeutically active agent is bicalutamide and is present in the implant in an amount of at least 30% v/v.

In various aspects, an implant of the disclosure may include bicalutamide in a total amount of at least 1 mg, for example, from about 1 mg to about 10 mg. In some cases, the total amount of bicalutamide in the implant may be from about 8 mg to about 10 mg. For example, the implant may include bicalutamide in a total amount of about 1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5.0 mg, about 5.1 mg, about 5.2 mg, about 5.3 mg, about 5.4 mg, about 5.5 mg, about 5.6 mg, about 5.7 mg, about 5.8 mg, about 5.9 mg, about 6.0 mg, about 6.1 mg, about 6.2 mg, about 6.3 mg, about 6.4 mg, about 6.5 mg, about 6.6 mg, about 6.7 mg, about 6.8 mg, about 6.9 mg, about 7.0 mg, about 7.1 mg, about 7.2 mg, about 7.3 mg, about 7.4 mg, about 7.5 mg, about 7.6 mg, about 7.7 mg, about 7.8 mg, about 7.9 mg, about 8.0 mg, about 8.1 mg, about 8.2 mg, about 8.3 mg, about 8.4 mg, about 8.5 mg, about 8.6 mg, about 8.7 mg, about 8.8 mg, about 8.9 mg, about 9.0 mg, about 9.1 mg, about 9.2 mg, about 9.3 mg, about 9.4 mg, about 9.5 mg, about 9.6 mg, about 9.7 mg, about 9.8 mg, about 9.9 mg, or about 10.0 mg.

In various aspects of the disclosure, the polymer material may be cured with the bicalutamide present therein. Without wishing to be bound by theory, curing refers to a chemical process that results in the hardening of a polymer material by cross-linking polymer chains. Any method may be used to cure a polymer of the disclosure, including the use of electron beams, heating, and/or the addition of additives. In various aspects of the disclosure, the bicalutamide may be mixed with an uncured polymer material prior to curing. In some aspects, the polymer matrix may be at least 95% cured, at least 96% cured, at least 97% cured, at least 98% cured, at least 99% cured, at least 99.9% cured, or 100% cured.

Generally, the polymer material has a curing temperature that is lower than the melting temperature of the therapeutically active agent, e.g., to prevent melting and/or degradation of the drug. For example, the polymer material may have a curing temperature that is lower than a melting temperature of bicalutamide. In some cases, polymer material may have a curing temperature that is lower than 190° C., lower than 185° C., lower than 180° C., lower than 175° C., lower than 170° C., lower than 165° C., lower than 160° C., lower than 155° C., or lower than 150° C. In a particular example, bicalutamide may have a melting temperature of about 180° C.-190° C., and the polymer may have a curing temperature of less than about 190° C. (e.g., about 170° C.).

In various aspects of the disclosure, the bicalutamide may be present in the implant in solid form. In some cases, the solid bicalutamide may be dissolved upon contact with biological fluids (e.g., after implantation into a tissue), and may diffuse out of the implant and into the target tissue. In some cases, the bicalutamide is present in the implant in crystalline form. In general, the particle size of the bicalutamide within the implant may be important for drug content uniformity within the implant. Without wishing to be bound by theory, a small particle size may ensure a uniform distribution within the formulation and between implants upon molding of the formulation. In some cases, the bicalutamide present in the implant may have a median particle size (e.g., D50 particle size) of less than 10 μm. In some cases, the bicalutamide present in the implant may have a D90 particle size of less than 15 μm.

In various aspects of the disclosure, the implant may further comprise additional molecules that are incapable of eluting from the implant. In some cases, these additional molecules may result in higher elution rates of the drug. Non-limiting examples of additional molecules that may be present within the implant include sugars (e.g., lactose), salts, fused silica, cellulose, and high molecular weight polyethylene glycol (PEG).

Generally, an implant of the disclosure has mechanical properties such that the implant can be successfully deployed into a target tissue. For example, an implant of the disclosure may be sufficiently stiff such that it can be deployed into a target tissue successfully, but not too stiff that it breaks during deployment. It should be understood that the mechanical properties of devices described herein may vary depending on the polymer material used, and may be determined empirically. In some aspects, the implant containing the bicalutamide may have a Shore A hardness of at least 30 durometer.

In various aspects, the implant may have a three-dimensional shape. The three-dimensional shape may be any suitable shape. In some cases, the implant may be cylindrical or substantially cylindrical. In some cases, the implant may be tubular or substantially tubular. In some cases, the implant may be elongate (e.g., may have a length greater than a width). In some cases, the implant may be not hollow. In some cases, the implant may be a rod or rod-like.

In various aspects, the implant may have a diameter. In some cases, a diameter of the implant may be from about 0.1 mm to about 1.5 mm. In some cases, a diameter of the implant may be from about 0.7 mm to about 1.3 mm. In some cases, a diameter of the implant may be from about 0.9 mm to about 1.1 mm. In some cases, a diameter of the implant may be at least about 0.1 mm, for example, at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1.0 mm, at least about 1.1 mm, at least about 1.2 mm, at least about 1.3 mm, at least about 1.4 mm, or at least about 1.5 mm. In some cases, a diameter of the implant may be less than about 1 mm, for example, less than about 1 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm. In some cases, a diameter of the implant may be at least about 0.1 mm. In some case, a diameter of the implant may be at least about 0.8 mm. In some cases, a diameter of the implant may be about 1 mm.

In various aspects, the implant may have a length. In some cases, a length of the implant may be from about 1 mm to about 30 mm. In some cases, a length of the implant may be from about 5 mm to about 25 mm. In some cases, a length of the implant may be from about 10 mm to about 20 mm. In some cases, a length of the implant may be from about 12 mm to about 18 mm. In some cases, a length of the implant may be at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, at least about 17 mm, at least about 18 mm, at least about 19 mm, at least about 20 mm, at least about 21 mm, at least about 22 mm, at least about 23 mm, at least about 24 mm, at least about 25 mm, at least about 26 mm, at least about 27 mm, at least about 28 mm, at least about 29 mm, or at least about 30 mm. In some cases, a length of the implant is at least about 1 mm. In some cases, a length of the implant is at least about 3 mm. In some cases, a length of the implant is about 15 mm. In some cases, a length of the implant may be less than about 30 mm, for example, less than about 30 mm, less than about 29 mm, less than about 28 mm, less than about 27 mm, less than about 26 mm, less than about 25 mm, less than about 24 mm, less than about 23 mm, less than about 22 mm, less than about 21 mm, less than about 20 mm, less than about 19 mm, less than about 18 mm, less than about 17 mm, less than about 16 mm, less than about 15 mm, less than about 14 mm, less than about 13 mm, less than about 12 mm, less than about 11 mm, less than about 10 mm, less than about 9 mm, less than about 8 mm, less than about 7 mm, less than about 6 mm, less than about 5 mm, less than about 4 mm, less than about 3 mm, less than about 2 mm, or less than about 1 mm.

In various aspects, the implant may have a volume. In some cases, the volume of the implant may be from about 0.1 mm$^3$ to about 30 mm$^3$. For example, the volume of the implant may be about 0.1 mm$^3$, about 0.5 mm$^3$, about 1 mm$^3$, about 5 mm$^3$, about 10 mm$^3$, about 15 mm$^3$, about 20 mm$^3$, about 25 mm$^3$, or about 30 mm$^3$. In some cases, the volume of the implant may be about 10 mm$^3$.

In various aspects, the implant may lack a coating, covering, or a sheath. For example, in some cases, a portion of the outer surface of the implant may not be coated or covered such that the outer surface of the uncoated or uncovered portion of the implant is directly exposed to or directly contacts the biological environment (e.g., a target tissue, a biological fluid) after implantation. In some examples, the entire outer surface or substantially the entire outer surface of the implant is uncovered or uncoated such that the entire outer surface or substantially the entire outer surface of the implant is directly exposed to or directly contacts a biological environment after implantation. In other cases, less than the entire outer surface of the implant is directly exposed to or directly contacts a biological environment after implantation. For example, in some cases, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the outer surface of the implant is directly exposed to or directly contacts a biological environment after implantation. In some cases, at least 50% of the outer surface of the implant is directly exposed to or directly contacts a biological environment after implantation. In some cases, the implant may lack a sheath, a scaffold, a retention member, a retention frame, or any other additional means for retaining the implant within the target tissue. In some cases, the implant may consist essentially of the polymer matrix and the therapeutically active agent (e.g., bicalutamide) dispersed therein.

In some cases, the implant may comprise a coating. In some cases, the coating may cover the implant. In some cases, the coating may partially cover the implant. In some cases, the coating may substantially cover the implant. In some cases, the implant may comprise a core made of a first polymer material, and a coating of a second polymer material. In a non-limiting example, an implant of the disclosure may include a non-silicone core, surrounded by a silicone coating. In some cases, an implant of the disclosure does not comprise a metal.

In various aspects, the implant may prevent modulation of the bicalutamide contained therein when the implant is implanted into a subject. Modulation can include, but is not limited to, degradation, chemical modification, and the like. For example, the biological environment of a tissue may include degradants that are capable of degrading the drug (e.g., esterases, amidases). In some cases, the implant may protect the therapeutically active agent from degradation by preventing the degradant from penetrating the implant. In various aspects, in vitro stability testing may be performed to determine the protective effect of the implant on the therapeutically active agent contained therein. For example, when the therapeutically active agent is bicalutamide, degradation may be determined by measuring the amount of the bicalutamide in an eluent after incubating the implant containing the bicalutamide in a solution comprising 1% SDS containing 0.05 N NaOH for 8 hours at 37° C. (e.g., in vivo stability testing, a non-limiting example of which has been provided in Example 2). In such cases, the therapeutically active agent may be capable of diffusing out of the implant while maintaining in vivo stability within the implant. In various aspects, the ability of a degradant to degrade a therapeutically active agent within the implant may be determined by a simulated in vivo stability assay, for example, as described in Example 2. In a non-limiting example, an implant of the disclosure comprising a therapeutically active agent may be incubated in a solution comprising a degradant (known to degrade the therapeutically active agent). After a period of incubation, the therapeutically active agent may be extracted from the implant and degradation peaks may be measured (e.g., by high-performance liquid chromatography (HPLC)).

In various aspects of the disclosure, an implant of the disclosure may be configured to be delivered directly to a target tissue of a subject. In some cases, the target tissue may be prostate tissue. In some cases, an implant of the disclosure may be configured to be delivered to a tissue adjacent to or nearby a target tissue. In some cases, the therapeutically active agent may diffuse out of the implant in a controlled manner and act directly on the target tissue.

In various aspects, an implant of the disclosure may be configured to remain within the target tissue for a period of time. In some cases, an implant of the disclosure may be configured to remain within the target tissue indefinitely (e.g., is never removed). In some cases, two or more implants of the disclosure may be implanted into the target tissue. For example, 2, 3, 4, 5, 6, 7, 8, 9, 10, 11, 12, 13, 14, 15, 16, 17, 18, 19, 20 or more than 20 implants may be implanted in the target tissue. In some cases, the two or more implants may be implanted in different sites of the target tissue (e.g., to deliver drug to different sites of the target tissue). In some cases, the two or more implants may be implanted in close proximity to one another within the target tissue. In some cases, one or more initial implants may be implanted, and additional implants may be later implanted after the drug has been exhausted from the initial implants. For example, one or more additional implants may be implanted after a drug has stopped, or substantially stopped, eluting from one or more initial implants. In some cases, an implant of the disclosure may be visible by ultrasound when disposed within the target tissue of the subject. In such cases, the position of the implant may be monitored non-invasively. In some cases, the implant may be sterilized prior to implantation into a subject. In some cases, the implant is sterilized via gamma sterilization.

In various aspects, an implant of the disclosure may be capable of delivering a sustained release of the therapeutically active agent for a period of time. For example, an implant of the disclosure may be capable of sustained release of the therapeutically active agent. "Sustained release" as used herein refers to the capability of the implant to release an amount of drug for an extended period of time after implantation into a target tissue. In some cases, an implant of the disclosure may be capable of delivering an amount of drug to a target tissue for at least 6 months, at least 9 months, at least 12 months, at least 18 months, or at least 24 months. In particular cases, an implant of the disclosure may be capable of delivering at least 0.1 μg/day of bicalutamide for at least 6 months after implantation into prostate tissue or tissue adjacent or near the prostate. In some cases, an implant of the disclosure may be capable of delivering at least 0.1 μg/day of bicalutamide (e.g., to a prostate) for up to 24 months after implantation into prostate tissue or tissue adjacent or near the prostate.

Methods for Manufacturing Drug Implants

Further provided herein are methods for manufacturing the implants described herein. A non-limiting example of a method for manufacturing a drug implant of the disclosure may be as provided in Example 1.

In some aspects, the methods may involve mixing an amount of uncured polymer material with an amount of a therapeutically active agent to form a mixture. The methods may further involve molding the mixture to create a molded structure. The methods may further involve curing the molded mixture by heating the molded mixture for a period of time. In some cases, the uncured polymer material may be any biocompatible silicone provided herein. In an exemplary aspect, the silicone may be Silbione® LSR D370 or DDU 4870 (as manufactured by NuSil™ (Trelyst)). In some cases, the therapeutically active agent may be an anti-androgen, examples of which have been provided herein. In an exemplary aspect, the therapeutically active agent may be bicalutamide.

The therapeutically active agent (e.g., bicalutamide) may be provided in the curing mixture in an amount such that a total amount of active agent in the implant may be from about 10% w/w to about 70% w/w, for example, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, or about 70% w/w. In some cases, the total amount of active agent in the implant may be at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, or at least about 70% w/w. In some cases, the therapeutically active agent is bicalutamide. The bicalutamide may be present within the curing mixture such that a total amount of bicalutamide in the implant is in an amount of at least 10% w/w, at least 30% w/w, at least 40% w/w, at least 45% w/w, or at least 60% w/w. The bicalutamide may be provided in the curing mixture in an amount such that a total amount of bicalutamide in the implant may be from about 1 mg to about 10 mg.

In some aspects, the curing comprises heating the molded mixture at 150° C. to 200° C., for example, 150° C., 155° C., 160° C., 165° C., 170° C., 175° C., 180° C., 185° C., 190° C., 195° C., or 200° C. The curing temperature generally depends on the polymer material selected. Generally, the curing temperature of the polymer material is selected such that it is lower than the melting temperature of the therapeutically active agent. In some cases, the curing comprises heating the molded mixture from 3 minutes to 8 minutes, for example, for 3 minutes, 4 minutes, 5 minutes, 6 minutes, 7 minutes, or 8 minutes. In some cases, the silicone and active agent may be selected based on the curing temperature of the silicone and the melting temperature of the active agent, such that the melting temperature of the active agent may be greater than the curing temperature of the silicone.

In some aspects, the mixture may further comprise a solvent. Non-limiting examples of solvents that may be used include pentane, heptane, toluene, dichloromethane, tetrahydrofuran, and hexane. In some aspects, the mixture may be molded by a transfer molding process.

After manufacturing the implant as provided herein, the methods may further comprise performing one or more analyses on the implant. In some cases, the one or more analyses may be differential scanning calorimetry (DSC), a non-limiting example of which has been provided in Example 2. In some cases, the one or more analyses may be deployment of the implant into surrogate tissue, a non-limiting example of which has been provided in Example 2. In some cases, the one or more analyses may be elution testing, a non-limiting example of which has been provided in Example 2. In some cases, the one or more analyses may be in vivo stability testing, a non-limiting example of which has been provided in Example 2. In some cases, the one or more analyses may be viscometry. In some cases, the one or more analyses may be high pressure liquid chromatography.

Methods of Treatment

Disclosed herein are methods of treating a disease (or a symptom thereof) in a subject. The terms "treating", "treatment", or "treat" may be used interchangeably herein and refer to providing a therapeutic benefit to a subject in need thereof. For example, treating a disease or disorder includes ameliorating, abrogating, reducing, relieving, or curing the disease or disorder. Treating a disease or disorder also includes ameliorating, abrogating, reducing, relieving, or curing one or more symptoms associated with a disease or disorder. When used in reference to a tumor, treating includes diminishing or reducing the size of the tumor or tumor volume.

In various aspects, the subject may have been diagnosed with, may be suspected of having, or may be at risk of having the disease. In some cases, the methods comprise implanting an implant of the disclosure into a target tissue of a subject. An implant of the disclosure may be implanted into a target tissue by any method. In some cases, the implant may be implanted into a target tissue by a surgical method or a non-surgical method. In some cases, the implant may be implanted using standard surgical tools, for example, tools commonly used for biopsies or brachytherapy. In some cases, the implant may be implanted into a target tissue by use of, e.g., a needle, forceps, a catheter (e.g., with a lumen). For example, in one embodiment, the implant may be implanted into a target tissue by deployment from the lumen of a needle or a catheter. In some cases, the implant may be implanted into a target tissue using a cannula of a prostate biopsy needle. In some cases, the implant may be implanted into a target tissue using a Mick® needle. In some cases, deployment of the implant may be guided by ultrasound. In some cases, the implant may be implanted by transperineal implantation (e.g., by use of a template guided needle). In some cases, the implant may be sterile and disposed within a packaging.

In a non-limiting example, a method of deploying an implant of the disclosure into a target tissue may involve disposing a distal end of an elongate tube into the target tissue (e.g., the prostate or tissue adjacent the prostate). In some cases, the elongate tube may be a needle having a lumen. The elongate tube may have a sharp end such that the distal end of the elongate tube can penetrate the target tissue. In some cases, the distal end of the elongate tube may be disposed through a first portion of a grid (e.g., a guide template) such that a first position of the elongate tube in the subject is determined. The grid may allow for proper placement of the implant into the target tissue. In some cases, a trocar is disposed within the lumen of the elongate tube. The methods may involve inserting the elongate tube (with or without a trocar disposed within a lumen of the elongate tube) into the target tissue. The methods may further involve, when using a trocar, removing the trocar from the lumen of the elongate tube, while maintaining the distal end of the elongate tube within the target tissue. The methods may further involve placing an implant of the disclosure within the lumen of the elongate tube. The implant may be pushed through the lumen of the elongate tube by a blunt-ended rod (e.g., a stylet) that is sized to fit within the lumen of the elongate tube. The stylet may be used to push the implant from a proximal end of the elongate tube to the distal end of the elongate tube. The methods may further involve, while maintaining the stylet in position, removing the elongate tube from the target tissue. As the elongate tube is removed from the target tissue, the stylet may push the implant out of the elongate tube and into the target tissue. The methods may further involve removing both the stylet and the elongate tube together from the target tissue.

In some aspects, the methods may involve implanting more than one implant into a target tissue of the subject. For example, the methods may involve implanting a first implant into a first portion of the target tissue, and a second implant into a second portion of the target tissue. In some cases, the first portion of the target tissue and the second portion of the target tissue may be different. In some cases, the first implant may comprise a first therapeutically active agent and the second implant may comprise a second therapeutically active agent. In some cases, the first therapeutically active agent and the second therapeutically active agent may be the same. In other cases, the first therapeutically active agent and the second therapeutically active agent may be different. In some cases, a grid (e.g., a guide template) may be used to position the first implant within the first portion of the target tissue, and to position the second implant within the second portion of the target tissue. In some cases, the first implant and/or the second implant may be positioned with the use of ultrasound guidance.

In some aspects, the methods may further comprise implanting additional implants into the target tissue. For example, the methods may further comprise implanting a third implant into a third portion of the target tissue, implanting a fourth implant into a fourth portion of the target tissue, implanting a fifth implant into a fifth portion of the target tissue, implanting a sixth implant into a sixth portion of the target tissue, implanting a seventh implant into a seventh portion of the target tissue, implanting an eighth implant into an eighth portion of the target tissue, and so forth. The third, fourth, fifth, sixth, seventh, eighth, or more, therapeutically active agents may each be the same, different, or combinations thereof. In some cases, at least three implants are implanted into a target tissue. For example, at least three implants may be implanted into the prostate or tissue adjacent or near the prostate by transperineal administration.

In some aspects, one or more implants may be implanted into a prostate or tissue adjacent or near a prostate prior to a surgical procedure to treat prostate cancer. For example, one or more implants may be implanted into a prostate or tissue adjacent or near a prostate prior to performing a prostatectomy (e.g., a week before, two weeks before, three weeks before, etc.). In such cases, the prostatectomy may remove the prostate or a portion thereof. In some cases, the prostatectomy may remove one or more of the implants from the subject. In other cases, one or more implants may be implanted into a prostate or tissue adjacent or near a prostate, and may remain in the prostate indefinitely. For example, the one or more implants may provide a therapeutically effective amount of bicalutamide to the prostate tissue for a period of time such that the subject is in remission or cured of the prostate cancer.

The term "subject", as used herein, generally refers to a vertebrate, such as a mammal, e.g., a human. Mammals include, but are not limited to, murines, simians, humans, research animals, farm animals, sport animals, and pets. In some cases, the methods described herein may be used on tissues derived from a subject and the progeny of such tissues. The tissues may be obtained from a subject in vivo. In some cases, the tissues may be cultured in vitro.

In some aspects, the methods provided herein may be used to treat a subject in need thereof. In some cases, the subject may suffer from a disease. In some cases, the subject may be a human. In some cases, the human may be a patient at a hospital or a clinic. In some cases, the subject may be a non-human animal, for example, a non-human primate, a livestock animal, a domestic pet, or a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a *lama*, a sheep, a goat, a buffalo, a reindeer, a yak, a mouse, a rat, a rabbit, or any other non-human animal.

In cases where the subject may be a human, the subject may be of any age. In some cases, the subject may be about 50 years or older. In some cases, the subject may be about 55 years or older. In some cases, the subject may be about 60 years or older. In some cases, the subject may be about 65 years or older. In some cases, the subject may be about 70 years or older. In some cases, the subject may be about 75 years or older. In some cases, the subject may be about 80 years or older. In some cases, the subject may be about 85 years or older. In some cases, the subject may be about 90 years or older. In some cases, the subject may be about 95 years or older. In some cases, the subject may be about 100 years or older. In some cases, the subject may be about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 years old. In some cases, the subject may be about 1, 2, 3, 4, 5, 6, 7, 8, 9, 10, 11, 12, 13, 14, 15, 16, 17, 18, 19, 20 or greater than 20 years old.

In some cases, the methods provided herein may treat a disease in a subject. In some cases, the methods provided herein may alleviate or reduce a symptom of a disease. In some cases, the methods provided herein may result in a reduction in the severity of one or more symptoms associated with a disease. In some cases, the methods provided herein may slow, halt, or reverse the progression of one or more symptoms associated with a disease. In some cases, the methods provided herein may prevent the development of one or more symptoms associated with a disease. In some cases, the methods provided herein may slow, halt, or reverse the progression of a disease, as measured by the number and severity of symptoms experienced.

In some cases, the disease may be a proliferative disease or disorder. In some cases, the proliferative disease or disorder may be cancer. In some cases, the subject may have a tumor. In some cases, the methods may reduce the size of a tumor. In some cases, the methods may reduce the size of a tumor by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or by 100%.

In some aspects, the proliferative disease or disorder may be a proliferative disease or disorder of the prostate. In one non-limiting example, the proliferative disease or disorder of the prostate may be prostate cancer. Prostate cancer can be adenocarcinoma, sarcoma, neuroendocrine tumors, small cell carcinoma, transitional cell carcinoma, or squamous cell carcinoma. In another non-limiting example, the proliferative disease or disorder of the prostate may be benign prostatic hyperplasia.

The methods may be employed to deliver a therapeutically effective amount of a drug to a target tissue. In some cases, the methods may involve delivering a drug implant to a target tissue (or a tissue adjacent to the target tissue) of the subject. Any tissue may be suitable for delivery of a drug implant of the disclosure. In exemplary cases, the target tissue may be the prostate, tissue adjacent to the prostate, or both. Non-limiting examples of target tissue includes breast, pancreas, bladder, brain, skin, kidney, lung, liver, tongue, esophagus, stomach, intestine, gallbladder, heart, pituitary gland, pineal gland, thyroid gland, parathyroid gland, adrenal gland, eye, bone, fallopian tubes, uterus, ovary, sinuses, inner ear (eustachian tube), testes, and neck.

In various aspects of the disclosure, the methods provide for implanting a drug implant of the disclosure into the target tissue (or an adjacent tissue) of a subject, wherein the implant delivers a therapeutically effective amount of the drug to the target tissue. As used herein, a "therapeutically effective amount" when used in reference to a drug or therapeutically active agent refers to an amount of drug or therapeutically active agent that is capable of eliciting a therapeutic response in a subject. In various aspects of the disclosure, the implant may deliver a therapeutically effective amount of drug to a tissue of the subject from 6 months to 24 months. In some cases, the implant may deliver a therapeutically effective amount of drug to a tissue of the subject for 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, or 24 months. In some cases, the implant may deliver a therapeutically effective amount of drug to a tissue of the subject for at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In various aspects of the disclosure, a therapeutically effective amount of drug may be at least 0.1 µg/day. In some cases, a therapeutically effective amount of drug may be at least 0.1 µg/day, 0.2 µg/day, 0.3 µg/day, 0.4 µg/day, 0.5 µg/day, 0.6 µg/day, 0.7 µg/day, 0.8 µg/day, 0.9 µg/day, 1 µg/day, 2 µg/day, 3 µg/day, 4 µg/day, 5 µg/day, 6 µg/day, 7 µg/day, 8 µg/day, 9 µg/day, 10 µg/day, 15 µg/day, 20 µg/day, 25 µg/day, 30 µg/day, 35 µg/day, 40 µg/day, 45 µg/day, 50 µg/day, 55 µg/day, 60 µg/day, 65 µg/day, 70 µg/day, 75 µg/day, 80 µg/day, 85 µg/day, 90 µg/day, 95 µg/day, 100 µg/day, 110 µg/day, 120 µg/day, 130 µg/day, 140 µg/day, 150 µg/day, 160 µg/day, 170 µg/day, 180 µg/day, 190 µg/day, 200 µg/day, 210 µg/day, 220 µg/day, 230 µg/day, 240 µg/day, 250 µg/day, 260 µg/day, 270 µg/day, 280 µg/day, 290 µg/day, 300 µg/day, 310 µg/day, 320 µg/day, 330 µg/day, 340 µg/day, 350 µg/day, 360 µg/day, 370 µg/day, 380 µg/day, 390 µg/day, 400 µg/day, 410 µg/day, 420 µg/day, 430 µg/day, 440 µg/day, 450 µg/day, 460 µg/day, 470 µg/day, 480 µg/day, 490 µg/day, 500 µg/day, 510 µg/day, 520 µg/day, 530 µg/day, 540 µg/day, 550 µg/day, 560 µg/day, 570 µg/day, 580 µg/day, 590 µg/day, 600 µg/day, 610 µg/day, 620 µg/day, 630 µg/day, 640 µg/day, 650 µg/day, 660 µg/day, 670 µg/day, 680 µg/day, 690 µg/day, 700 µg/day, 710 µg/day, 720 µg/day, 730 µg/day, 740 µg/day, 750 µg/day, 760 µg/day, 770 µg/day, 780 µg/day, 790 µg/day, 800 µg/day, 810 µg/day, 820 µg/day, 830 µg/day, 840 µg/day, 850 µg/day, 860 µg/day, 870 µg/day, 880 µg/day, 890 µg/day, 900 µg/day, 910 µg/day, 920 µg/day, 930 µg/day, 940 µg/day, 950 µg/day, 960 µg/day, 970 µg/day, 980 µg/day, 990 µg/day, 1000 µg/day or greater. It should be understood that a therapeutically effective amount of drug may vary based on the drug and/or the disease to be treated, and may be determined empirically.

In various aspects, the implant may result in cumulative release of the therapeutically active agent from the implant into the target tissue. In some cases, the cumulative release of bicalutamide from the implant in vitro may be at least 100 µg on day 1. In some cases, the cumulative release of bicalutamide from the implant in vitro may be at least 1,500 µg on day 50. In some cases, the cumulative release of bicalutamide from the implant in vitro may be at least 2,000 µg on day 100. In some cases, at least 50% of the total amount of bicalutamide present within the implant at the time of implantation remains in the polymer matrix at 100 days post-implantation.

In various aspects of the disclosure, the implant may be configured to remain within the target tissue for a period of time. In some cases, the implant may be configured to remain within the target tissue for long periods of time (e.g., months to years) or indefinitely (e.g., may never be removed). For example, after the implant has delivered all of the therapeutically active agent contained therein to the subject, the implant (devoid of the therapeutically active agent) may remain within the target tissue. In some cases, if additional treatment is needed, one or more additional implants may be delivered to the target tissue (without removing the initial implant). In some cases, the implant may be composed of a non-biodegradable and/or non-resorbable polymer material such that the polymer material remains substantially intact within the target tissue for long periods of time or indefinitely.

Advantageously, the implants of the disclosure are capable of delivering a therapeutically effective amount of bicalutamide to the prostate tissue, or tissue adjacent or near the prostate, for extended periods of time (e.g., at least 6 months). Additionally, the implants of the disclosure are capable of delivering a high concentration of bicalutamide locally to the prostate, while maintaining low systemic concentrations of bicalutamide. In some cases, the implants of the disclosure may reduce or prevent toxicity due to high systemic concentrations of bicalutamide.

In various aspects, a total dose of bicalutamide administered to the subject by an implant of the disclosure is less than a total dose of bicalutamide when administered to a subject by systemic (e.g., oral) administration. Standard oral dosing regimens of bicalutamide include 150 mg/day bicalutamide monotherapy for early stage prostate cancer, and 50 mg/day in combination with other therapies for advanced prostate cancers. Advantageously, the implants of the disclosure provide for administration of lower total doses of bicalutamide relative to oral dosing regimens. In some cases, the total amount of bicalutamide administered to a subject is less than 100 mg over a 6 month period.

In various aspects, implanting a drug implant of the disclosure into the prostate or tissue adjacent or near the prostate results in a blood plasma concentration of bicalutamide that is substantially less than a blood plasma concentration of bicalutamide obtained when bicalutamide is administered to a subject by systemic (e.g., oral) administration. For example, the steady state blood plasma concentration of R-enantiomer of bicalutamide has been reported to be about 9 µg/ml. In some cases, an implanting an implant of the disclosure into the prostate or tissue adjacent or near the prostate results in a steady state blood plasma concentration of R-bicalutamide that is less than 9 µg/ml, for example, less than 5 µg/ml.

Kits

Further provided herein are kits. In some aspects, a kit may comprise one or more implants as described herein. For example, a kit may include 1, 2, 3, 4, 5, 6, 7, 8, 9, 10, 11, 12, 13, 14, 15, 16, 17, 18, 19, 20 or more than 20 implants. In some cases, the one or more implants may comprise a therapeutically active agent contained therein. In some cases, each of the one or more implants may comprise the same therapeutically active agent. In other cases, each of the one or more implants may comprise one or more different therapeutically active agents.

In some aspects, a kit may comprise one or more surgical tools, such as a needle or forceps. In some aspects, a kit may be packaged in a sterilized package. In some cases, the sterilized package comprises a foil. In some aspects, a kit may further comprise instructions for implanting the implant into a tissue of a subject.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed.

In this application, the use of the singular includes the plural unless specifically stated otherwise. It must be noted that, as used in the specification and the appended claims, the singular forms "a," "an", and "the" include plural referents unless the context clearly dictates otherwise. In this application, the use of "or" means "and/or" unless stated otherwise. Furthermore, use of the term "including" as well as other forms, such as "include", "includes", and "included", is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error, e.g., within 15%, 10%, or 5%.

The section headings used herein are for organizational purposes only and are not to be construed as limiting the subject matter described.

Non-Limiting List of Exemplary Embodiments

In addition to the aspects and embodiments described and provided elsewhere in this disclosure, the following non-limiting list of particular embodiments are specifically contemplated.

1. An implant comprising:
    a biocompatible, substantially non-biodegradable polymer matrix; and
    an anti-androgen dispersed throughout the polymer matrix.
2. An implant comprising:
    a biocompatible polymer matrix; and
    a therapeutically active agent dispersed throughout the polymer matrix, wherein the implant delivers a therapeutically effective amount of the therapeutically active agent to a target tissue of a subject for at least 24 months when the implant is disposed in the target tissue of the subject.
3. An implant comprising:
    a biocompatible, substantially non-biodegradable polymer matrix; and
    an anti-androgen in crystalline form.
4. An implant comprising:
    a biocompatible, substantially non-biodegradable polymer matrix; and an anti-androgen dispersed throughout the polymer matrix at an amount from 10 to 70% w/w.
5. The implant of any one of embodiments 1-4, wherein the implant, when disposed in the target tissue of the subject, releases at least 0.1 µg/day of the therapeutically active agent or the anti-androgen at 24 months after implantation.
6. The implant of any one of embodiments 1-5, wherein the therapeutically active agent or the anti-androgen has a median particle size of less than 10 microns.
7. The implant of any one of embodiments 1-6, wherein the implant has a Shore A hardness of at least 30 durometer when loaded with 60% w/w of a therapeutically active agent.
8. The implant of any one of embodiments 1-7, wherein at least 99% of the polymer matrix remains in the target tissue of the subject after implantation for at least 600 days.
9. The implant of any one of embodiments 1-8, wherein the implant is visible by ultrasound when disposed in the target tissue of the subject.
10. The implant of any one of embodiments 1-9, wherein the therapeutically active agent or the anti-androgen has a melting temperature that is greater than a curing temperature of the polymer matrix.
11. The implant of embodiment 10, wherein the melting temperature is greater than 150° C.
12. The implant of any one of embodiments 1-11, wherein the polymer matrix inhibits degradation of the therapeutically active agent or the anti-androgen in the implant.
13. The implant of embodiment 12, wherein the polymer matrix inhibits degradation of the therapeutically active agent or the anti-androgen by an esterase or an amidase.
14. The implant of embodiment 12 or 13, wherein the degradation is determined by measuring the amount of the therapeutically active agent or the anti-androgen in an eluent after incubating the implant containing the therapeutically active agent or the anti-androgen in a solution comprising 1% SDS containing 0.05 N NaOH for 8 hours at 37° C.
15. The implant of any one of embodiments 1-14, wherein the implant is elongate.
16. The implant of any one of embodiments 1-15, wherein the implant is cylindrical.
17. The implant of any one of embodiments 1-15, wherein the implant is tubular.
18. The implant of any one of embodiments 1-17, wherein a diameter of the implant is less than 1 mm.
19. The implant of any one of embodiments 1-18, wherein a diameter of the implant is from 0.5 mm to 1.5 mm.
20. The implant of any one of embodiments 1-18, wherein a diameter of the implant is from 0.7 mm to 1.3 mm.
21. The implant of any one of embodiments 1-18, wherein a diameter of the implant is from 0.9 mm to 1.1 mm.
22. The implant of any one of embodiments 1-18, wherein a diameter of the implant is about 1 mm.
23. The implant of any one of embodiments 1-22, wherein a length the implant is less than 20 mm.
24. The implant of any one of embodiments 1-22, wherein a length of the implant is from 5 mm to 25 mm.
25. The implant of any one of embodiments 1-22, wherein a length of the implant is from 10 mm to 20 mm.
26. The implant of any one of embodiments 1-22, wherein a length of the implant is from 12 mm to 18 mm.
27. The implant of any one of embodiments 1-22, wherein a length of the implant is about 15 mm.
28. The implant of any one of embodiments 1-27, wherein the implant further comprises a coating.
29. The implant of embodiment 28, wherein the coating partially covers the implant.
30. The implant of embodiment 28, wherein the coating substantially covers the implant.
31. The implant of embodiment 28, wherein the coating covers the implant.
32. The implant of embodiment 2, wherein the therapeutically active agent is an anti-androgen.
33. The implant of any one of embodiments 1-32, wherein the therapeutically active agent or the anti-androgen is bicalutamide.
34. The implant of any one of embodiments 1-33, wherein the implant is sterile.
35. The implant of any one of embodiments 1-34, wherein the implant is disposed in a sterilized package.
36. The implant of any one of embodiments 1-35, wherein the polymer matrix is at least 95% cured, at least 96% cured, at least 97% cured, at least 98% cured, at least 99% cured, or at least 99.9% cured.
37. The implant of any one of embodiments 1-36, wherein the polymer matrix comprises silicone.
38. The implant of embodiment 37, wherein the silicone is Silbione® LSR D370 as manufactured by Elkem.
39. The implant of embodiment 37, wherein the silicone is DDU 4870 as manufactured by NuSil™.
40. The implant of any one of embodiments 1-39, wherein the implant is configured to be implanted into prostate tissue of a subject.
41. The implant of any one of embodiments 1-40, wherein the implant lacks a metal.
42. A method of manufacturing an implant suitable for implantation into the prostate of a subject, the method comprising:
    (a) mixing an amount of uncured biocompatible, substantially non-biodegradable polymer with an amount of anti-androgen to form a mixture;
    (b) molding the mixture to create a molded mixture; and
    (c) curing the molded mixture by heating the molded mixture for a period of time.
43. The method of embodiment 42, wherein the amount of anti-androgen is between 10% w/w and 70% w/w of the uncured biocompatible, substantially non-biodegradable polymer.
44. The method of embodiment 42 or 43, wherein the anti-androgen is bicalutamide.
45. The method of any one of embodiments 42-44, wherein the biocompatible, substantially non-biodegradable polymer is a silicone.
46. The method of embodiment 45, wherein the silicone is Silbione® LSR D370 as manufactured by Elkem.
47. The method of embodiment 45, wherein the silicone is DDU 4870 as manufactured by NuSil™.
48. The method of any one of embodiments 42-47, wherein the curing of (c) further comprises heating the molded mixture at a temperature from about 150° C. to about 200° C. for 3 to 8 minutes.
49. The method of any one of embodiments 42-48, wherein the mixture further comprises a solvent.
50. The method of embodiment 49, wherein the solvent is selected from the group consisting of: pentane, dichloromethane, tetrahydrofuran, heptane, toluene, and hexane.

51. The method of any one of embodiments 42-50, wherein the mixture is molded by a transfer molding process.
52. The method of any one of embodiments 42-51, further comprising, performing an analysis on the implant.
53. The method of embodiment 54, wherein the analysis is selected from the group consisting of: differential scanning calorimetry (DSC), deployment of implant in surrogate tissue, elution testing, viscometry, high pressure liquid chromatography (HPLC), and simulated in vivo stability assay.
54. A kit comprising:
   a sterilized package comprising an implant according to any one of embodiments 1-41 therein; and
   instructions for implanting the implant into a target tissue of a subject.
55. The kit of embodiment 54, wherein the implant is configured for delivery into a human prostate, tissue adjacent the human prostate, or both.
56. The kit of embodiment 54 or 55, wherein the sterilized package is formed from a foil.
57. The kit of any one of embodiments 54-56, further comprising one or more surgical tools for implanting the implant into the target tissue of the subject.
58. The kit of embodiment 57, wherein the one or more surgical tools comprises a needle, forceps, a trocar, or a stylet.
59. A method of treating a disease in a subject in need thereof, comprising:
   implanting an implant of any one of embodiments 1-41 into the prostate of the subject, thereby treating the disease.
60. A method of treating a disease in a subject in need thereof, comprising:
   implanting a substantially non-biodegradable implant comprising a biocompatible polymer matrix and an anti-androgen drug dispersed throughout the biocompatible polymer matrix into the prostate of the subject, thereby treating the disease.
61. The method of embodiment 60, wherein the prostate comprises prostate tissue, tissue adjacent the prostate tissue, or both.
62. The method of embodiment 60 or 61, wherein the disease is a proliferative disease or disorder of the prostate (e.g., prostate cancer, benign prostatic hyperplasia).
63. The method of any one of embodiments 60-62, further comprising disposing a distal end of an elongate tube in the subject's prostate or tissue adjacent the prostate.
64. The method of embodiment 63, wherein a portion of the elongate tube is disposed through a first portion of a grid such that a first position of the elongate tube in the subject is determined.
65. The method of embodiment 63 or 64, wherein the elongate tube is a needle or a catheter.
66. The method of embodiment 65, wherein a trocar is disposed within a lumen of the elongate tube.
67. The method of embodiment 66, further comprising removing the trocar from the lumen of the elongate tube.
68. The method of embodiment 67, further comprising, after removing the trocar from the lumen of the elongate tube, positioning the implant within the lumen of the elongate tube.
69. The method of embodiment 68, further comprising pushing a stylet through the lumen of the elongate tube, thereby displacing the implant to the distal end of the elongate tube.
70. The method of embodiment 69, further comprising displacing the elongate tube away from the subject such the implant remains within the subject.
71. The method of embodiment 70, wherein the stylet is disposed in a portion of the lumen of the elongate tube, a distal end of the stylet adjacent the implant such that the implant remains within the subject.
72. The method of any one of embodiments 60-71, wherein a portion of a second elongate tube is disposed through a second portion of the grid such that a position of the second elongate tube in the subject is determined.

EXAMPLES

Example 1. Methods for Making Implants

Manufacture of the implant included two main steps: formulation of the active pharmaceutical ingredient (API) (e.g., bicalutamide) with an elastomer (e.g., heat cured silicone) to ensure uniform mixing of the API within the polymer matrix, and molding of the implants to ensure the product can be deployed to the organ as intended.

Formulation

The implant formulation included medical grade silicone as an excipient mixed with the API. A solvent was used for reducing the viscosity of the silicone, if needed, to incorporate the desired API loading.

The 60% w/w bicalutamide formulation was made using a centrifugal mixer (FlackTek DAC400-VAC). The required amount of silicone Part A and Part B were added to the mixing cup and an equal weight of a solvent (that dissolves silicone; e.g., pentane) was added. The silicone and solvent were speed-mixed until the viscosity of the silicone was reduced such that it flowed. The API powder was then incorporated into the mixing cup and speed-mixed until a visibly smooth mixture was obtained with no dry API spots. The solvent was then removed under vacuum leaving a paste of silicone and API. Table 1 below shows the formulation for 60% w/w bicalutamide using Silbione® LSR D370 as the silicone and pentane as a solvent for a 10-gram mix. Table 2 below lists a set of solvent removal parameters which can be repeated until the desired amount of solvent is removed as confirmed by weight.

Other methods to achieve the same mix uniformity that are solvent-less may be used, such as shear mixing. Other solvents (e.g., dichloromethane, tetrahydrofuran, hexane, pentane, heptane, toluene, and the like) that aid in reduction of viscosity and dissolve silicone may also be used for formulation.

TABLE 1

Example Formulation Composition 60% w/w Bicalutamide

| Component | Weight Added (g) |
| --- | --- |
| Silbione ® LSR D370 Part A | 2 |
| Silbione ® LSR D370 Part B | 2 |
| Solvent | 4 |
| Bicalutamide Milled Powder | 6 |

TABLE 2

Example Solvent Removal Conditions

| Solvent Removal Cycle | Step | Speed (RPM) | Time (min) | Vacuum (psi) |
|---|---|---|---|---|
| 1 | 1 | 950 | 1.8 | 9.0 |
|   | 2 | 950 | 0.3 | 14.7 |
|   | 3 | 1450 | 1.8 | 3.9 |
| 2 | 1 | 1950 | 2.8 | 3.9 |
|   | 2 | 1950 | 2.8 | 3.9 |
|   | 3 | 1950 | 2.8 | 3.9 |
|   | 4 | 1950 | 2.8 | 3.9 |
| 3 | 1 | 800 | 2.8 | 0.14 |
|   | 2 | 2400 | 0.3 | 0.14 |
|   | 3 | 950 | 2.8 | 0.14 |

Molding

Implant rods were made using an aluminum mold via a transfer molding process. The molds were assembled, and a pre-weighed amount of the formulation was injected into the mold. Post-formulation injection, the rods were cured for a predetermined time (3 to 8 minutes) at a certain temperature (150 to 200° C.) based on the silicone supplier's recommendations for curing. Post-curing, the mold was cooled, and the rods were de-molded for characterization. FIG. 1 depicts an example of a molded implant according to Example 1.

Example 2. Characterization of Bicalutamide Containing Formulation and Implants

Various analytical techniques were used for characterization of the formulation and molded implants. Differential Scanning calorimetry (DSC) was used to determine the rate of curing of the implants and to confirm that crystalline properties of the drug were not impacted. Deployment of implant in cow tongue was used to assess adequate deployment of the implant due to its tissue properties which are comparable to the prostate. The method for deployment is described. Elution Testing was used to assess the rate of elution of drug from the implant. A viscometer was used to assess the viscosity and curing profile for the formulation to confirm that process parameters used are capable of molding cured rods. High Pressure Liquid Chromatography (HPLC) was used to confirm content uniformity and assess impurities in the drug formulation and molded rods. Simulated in vivo stability assay was used to assess the ability of degradants to penetrate the implant.

Differential Scanning Calorimetry (DSC)

Samples were run on a TA Instruments Model Q2000 (V24.11 Build 124) DSC equipped with a nitrogen flow sample chamber. Samples were prepared by loading ~5-15 mg of material into a hermetically sealed aluminum Tzero pan. The samples were placed on the DSC sampler and run under a nitrogen purge (50 mL/min) at a rate of 10° C./min from 20° C. to 220° C. FIGS. 2A-2F show a set of DSC thermograms that were generated during development. A comparison of the thermogram of uncured silicone (FIG. 2A) to an in-process formulation mix (FIG. 2C) and the molded rod (FIGS. 2B and 2D) shows that the molded rods were fully cured and that the API was mixed into the formulation. A comparison of the thermogram for API alone (FIG. 2E) and the molded rods at 45% w/w API (FIG. 2F) and 60% w/w API (FIG. 2D) showed no change in the melting range for the API (191 to 193° C.) indicating that the crystalline structure of the API was likely not altered during formulation and molding.

Implant Deployment

Figure 3A:
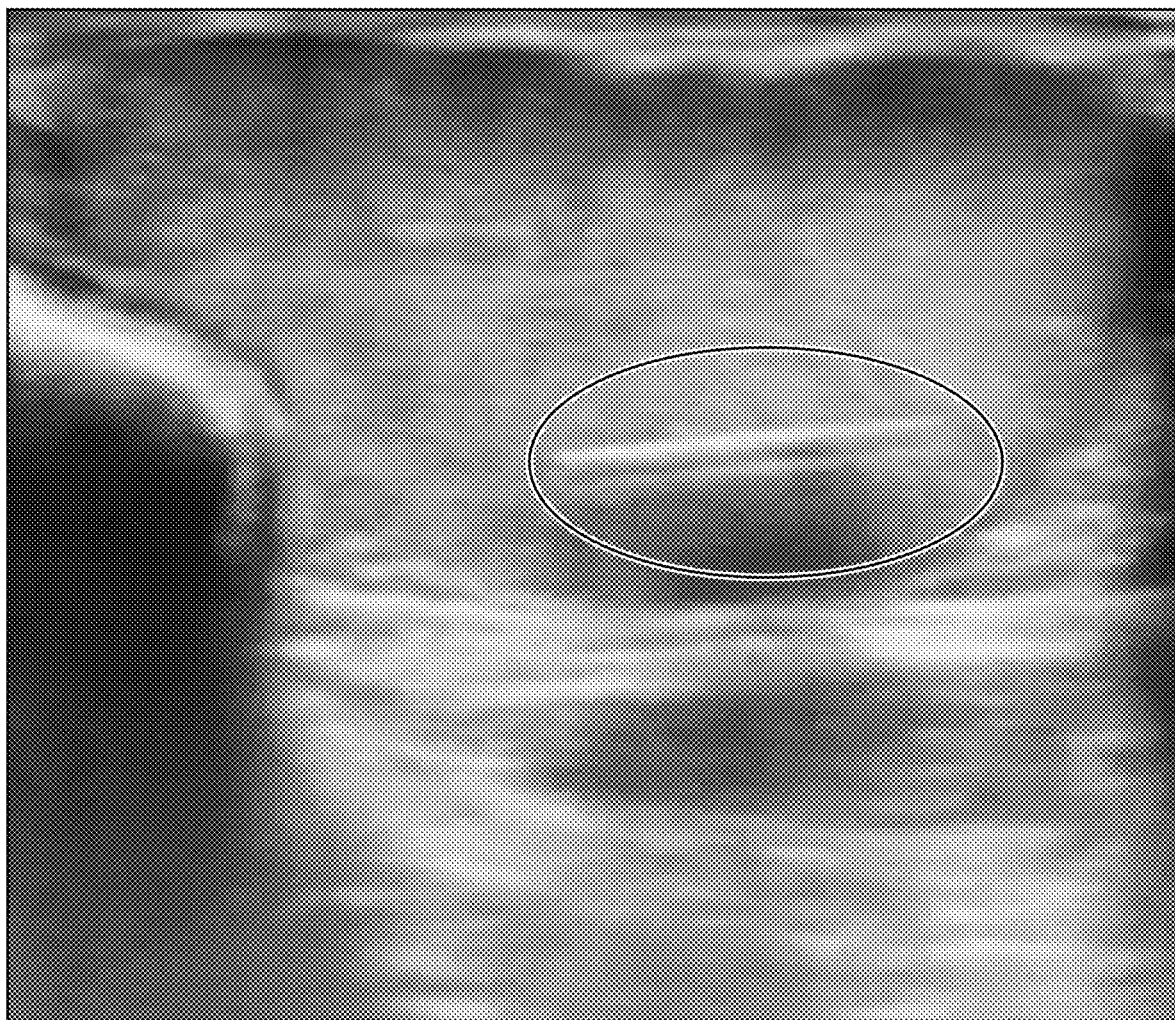
FIG. 3A, FIG. 3B, and FIG. 3C depict non-limiting examples of ultrasound images of an implant in dog prostate (FIG. 3A and FIG. 3B) and a picture of an explant 8 weeks post implantation (FIG. 3C) according to aspects of the disclosure.
Figure 3B:
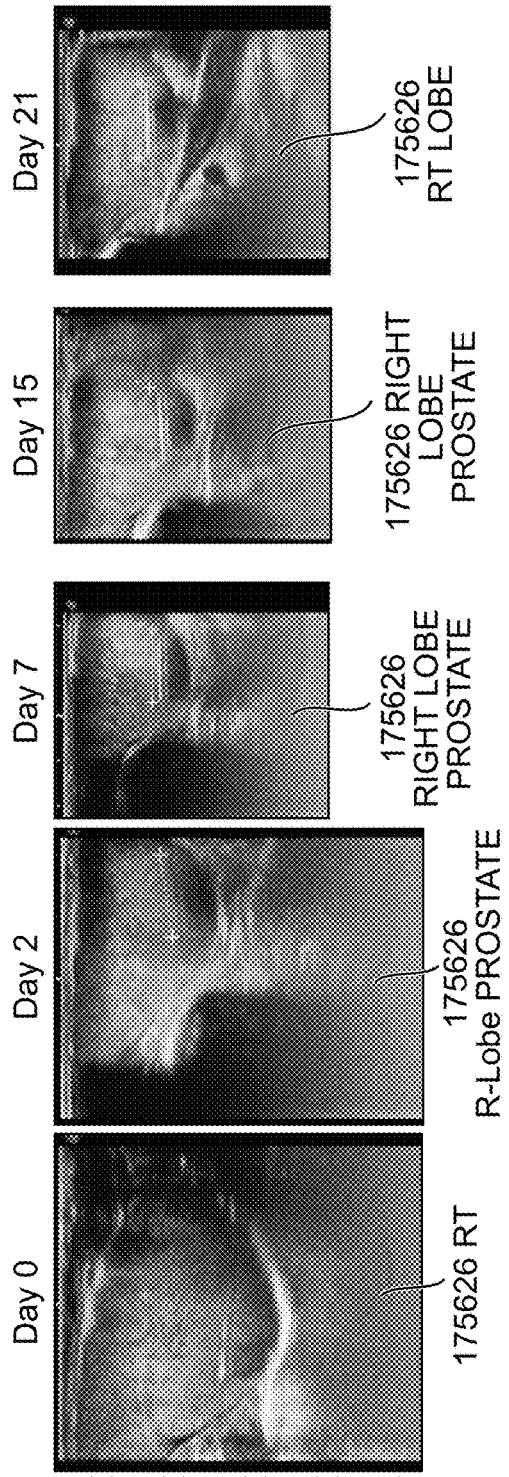
Figure 3C:
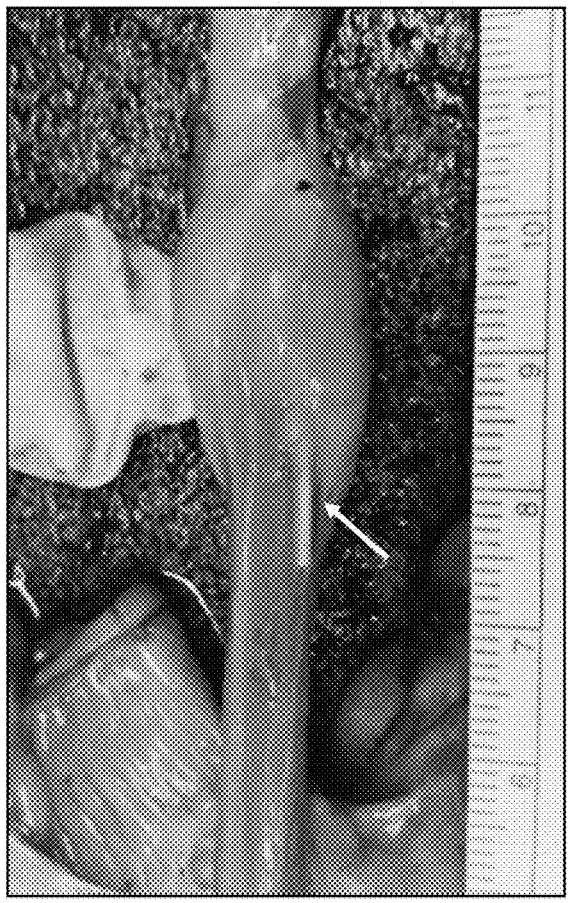

The drug implant was deployed into the prostate of dogs. To date, two pre-clinical studies in dogs have been performed and the data from these studies has shown that the implant can be successfully implanted in the prostate and remains within the prostate for at least 8 weeks (FIGS. 3A-3C).

Elution Testing

Figure 4A:
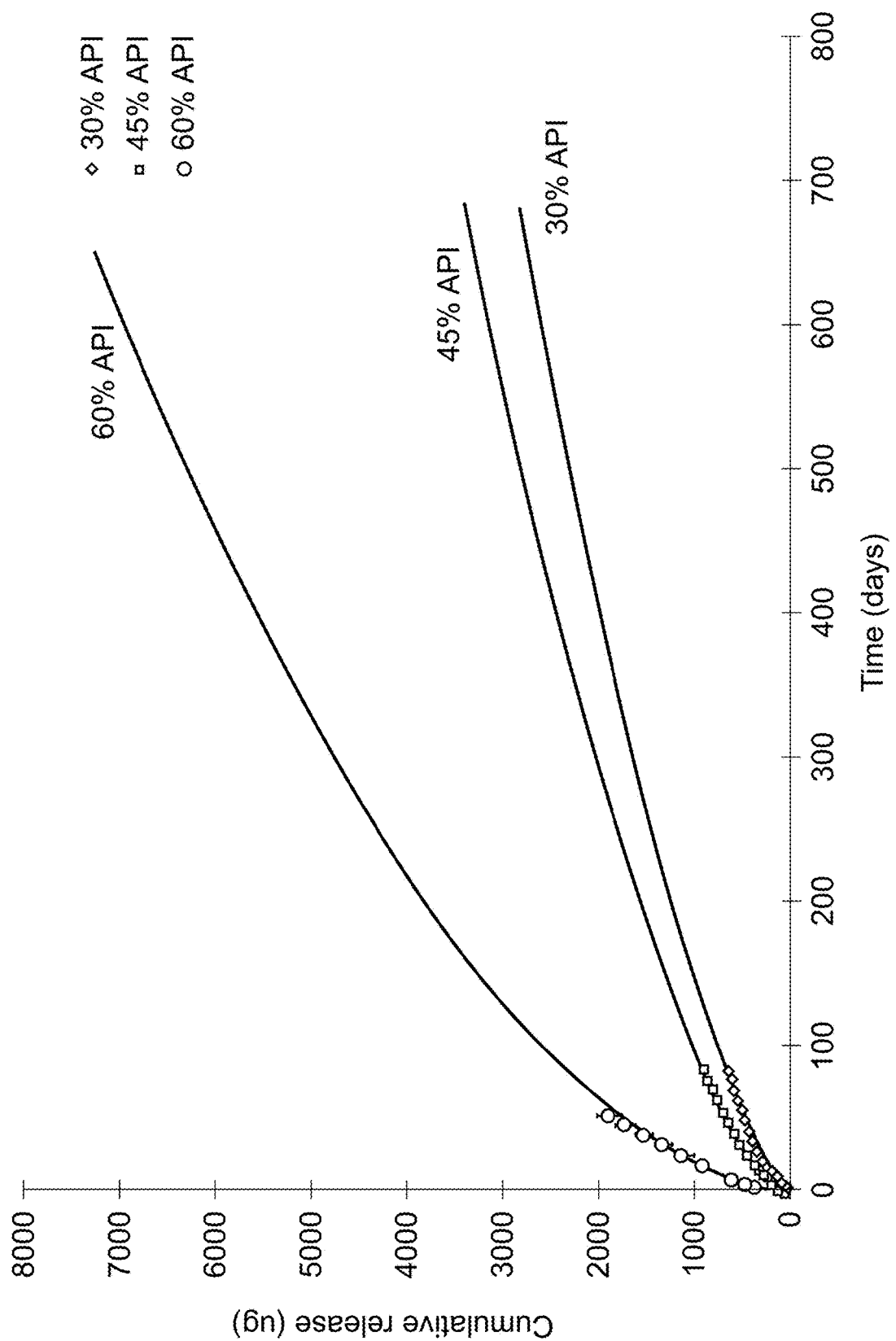
FIG. 4A depicts non-limiting examples of in vitro elution curves for 30% w/w, 45% w/w, and 60% w/w bicalutamide implants according to aspects of the disclosure.
Figure 4B:
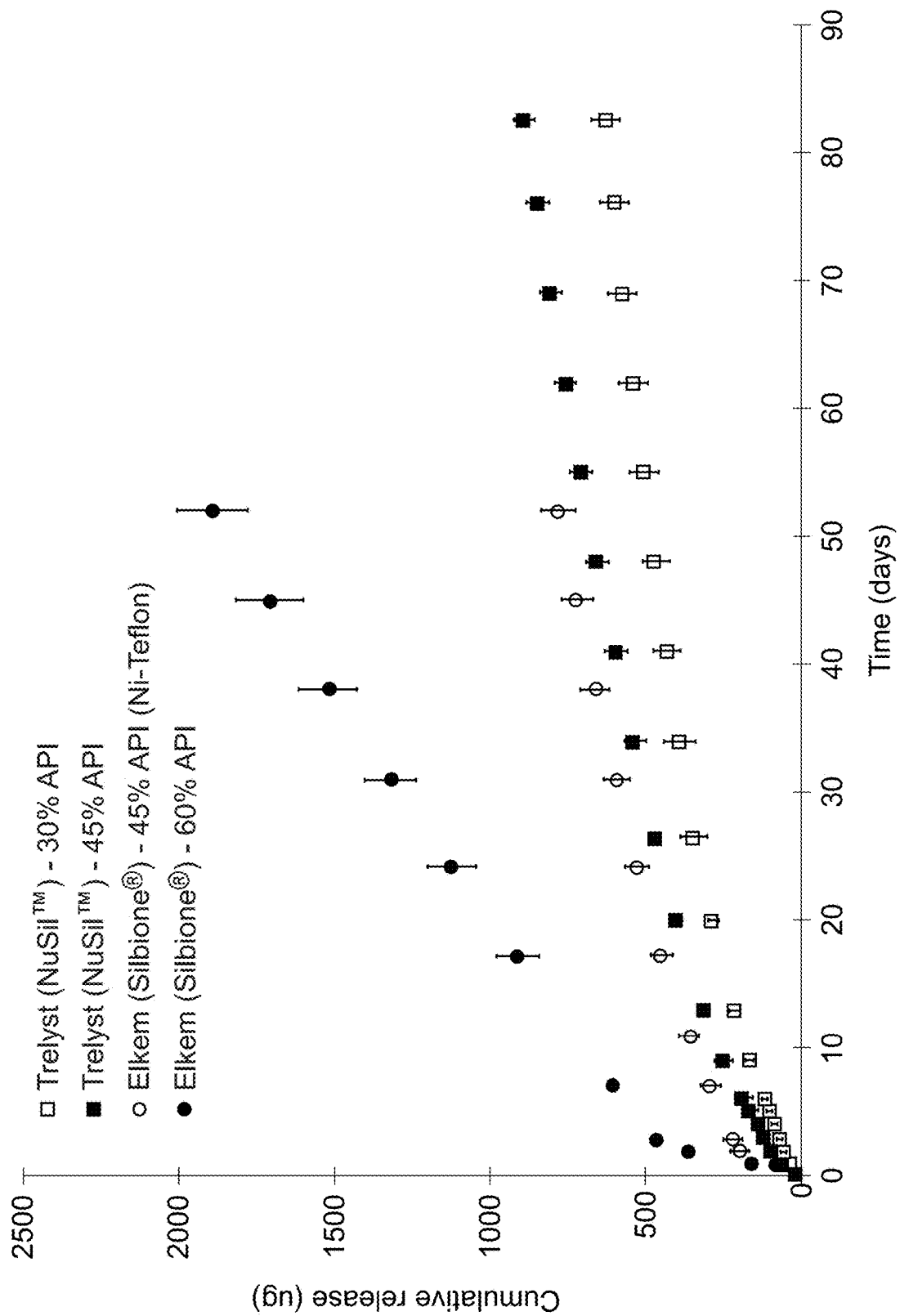
FIG. 4B depicts non-limiting examples of in vitro elution curves for 30% w/w and 45% w/w bicalutamide with various silicone implants.
Figure 4C:
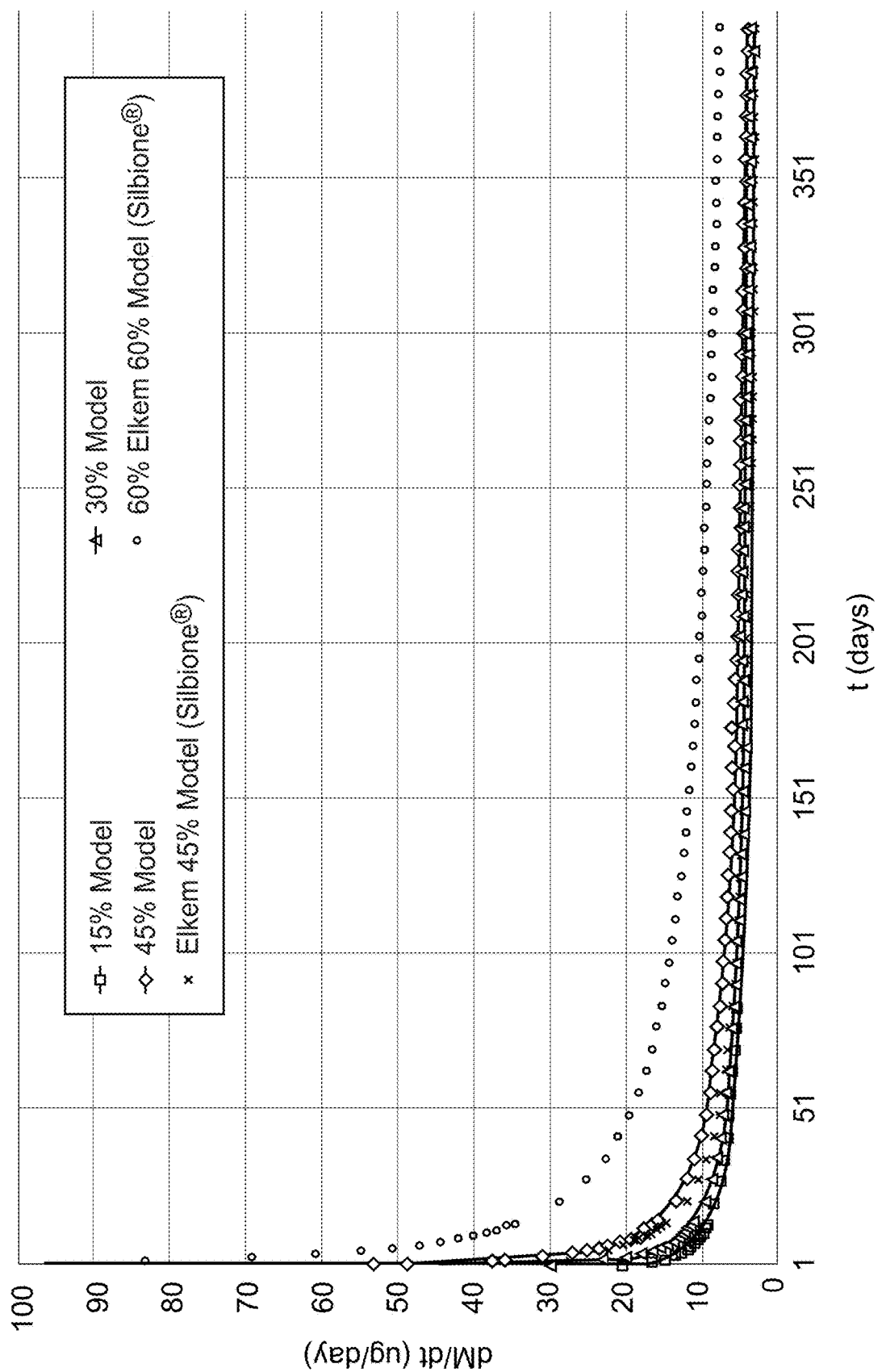
FIG. 4C depicts projected elution curves for bicalutamide-loaded implants up to 24 months.

Elution testing was performed to analyze the in vitro performance of the molded implant. Implants were placed in a 1% w/w sodium lauryl sulfate (SDS) solution and the elution media was replaced at regular intervals. The eluent of API was quantitated at each timepoint via UV/Vis Spectroscopy or HPLC. A comparison of elution curves for a 30% w/w, 45% w/w, and 60% w/w bicalutamide formulation along with the predicted profile out to ~2 years is shown in FIGS. 4A-4C.

Figure 4D:
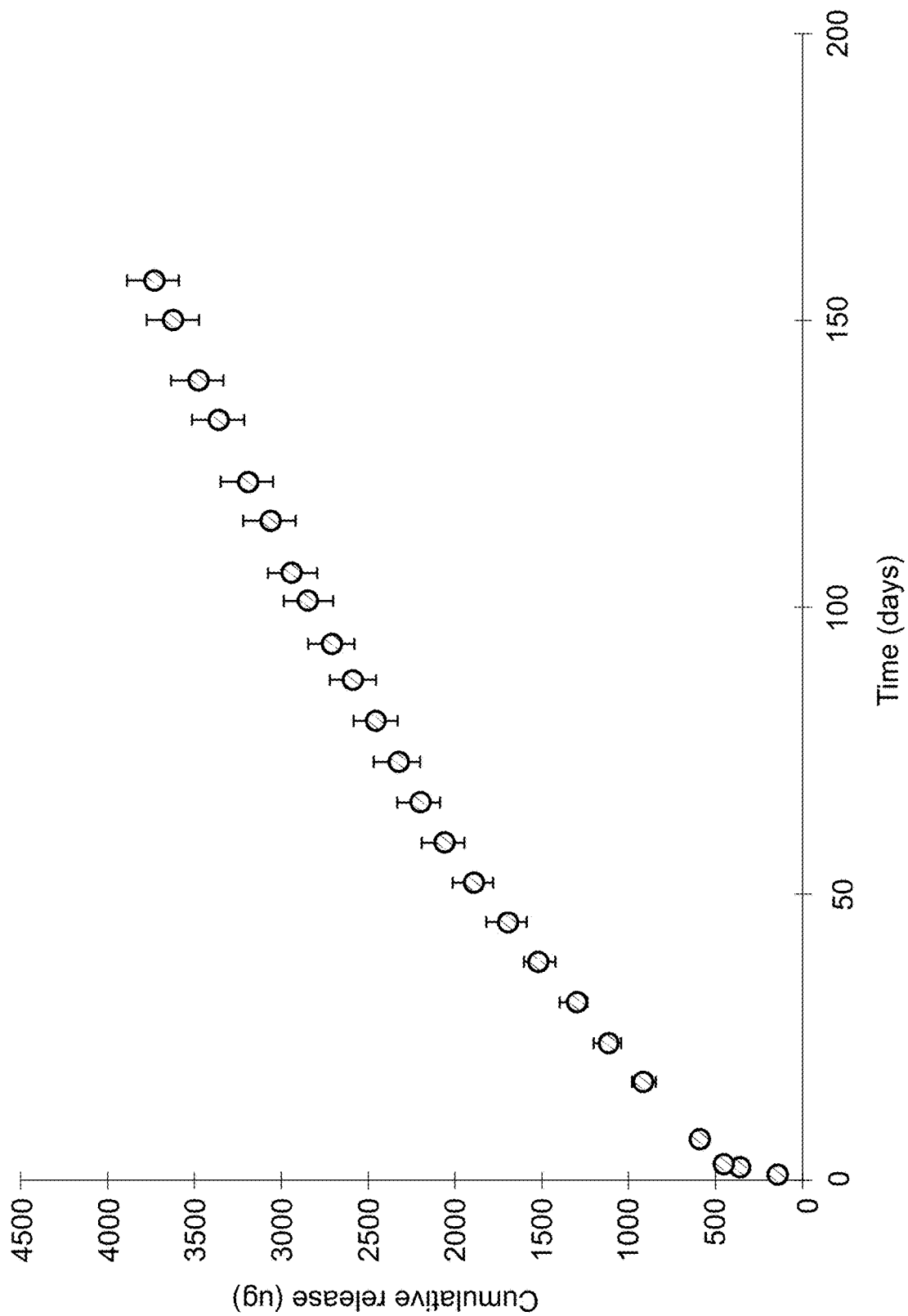
FIG. 4D depicts a cumulative release profile of an implant containing 60% w/w bicalutamide in an in vitro model.
Figure 4E:
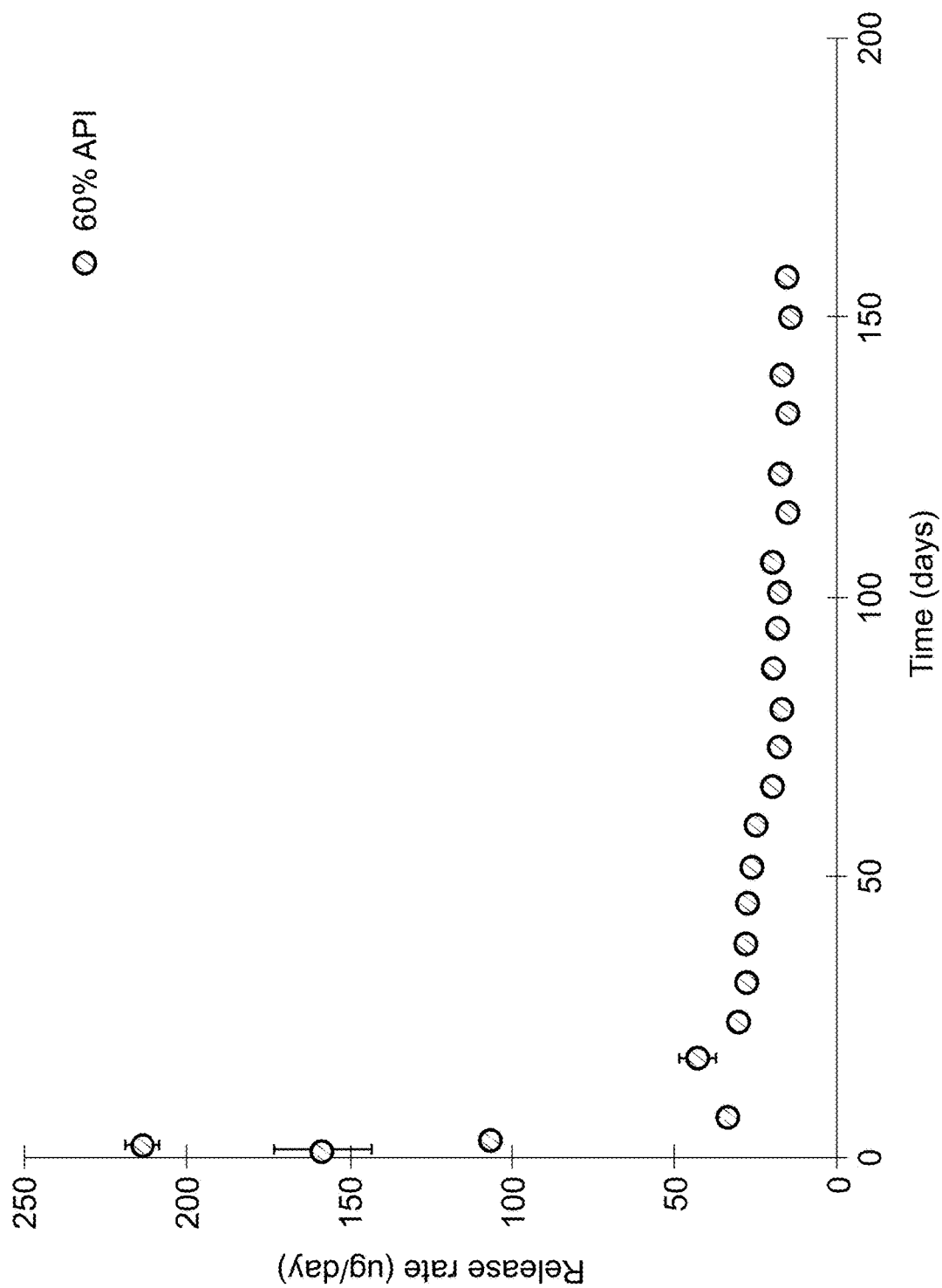
FIG. 4E depicts a release rate profile of an implant containing 60% w/w bicalutamide in an in vitro model.
Figure 4F:
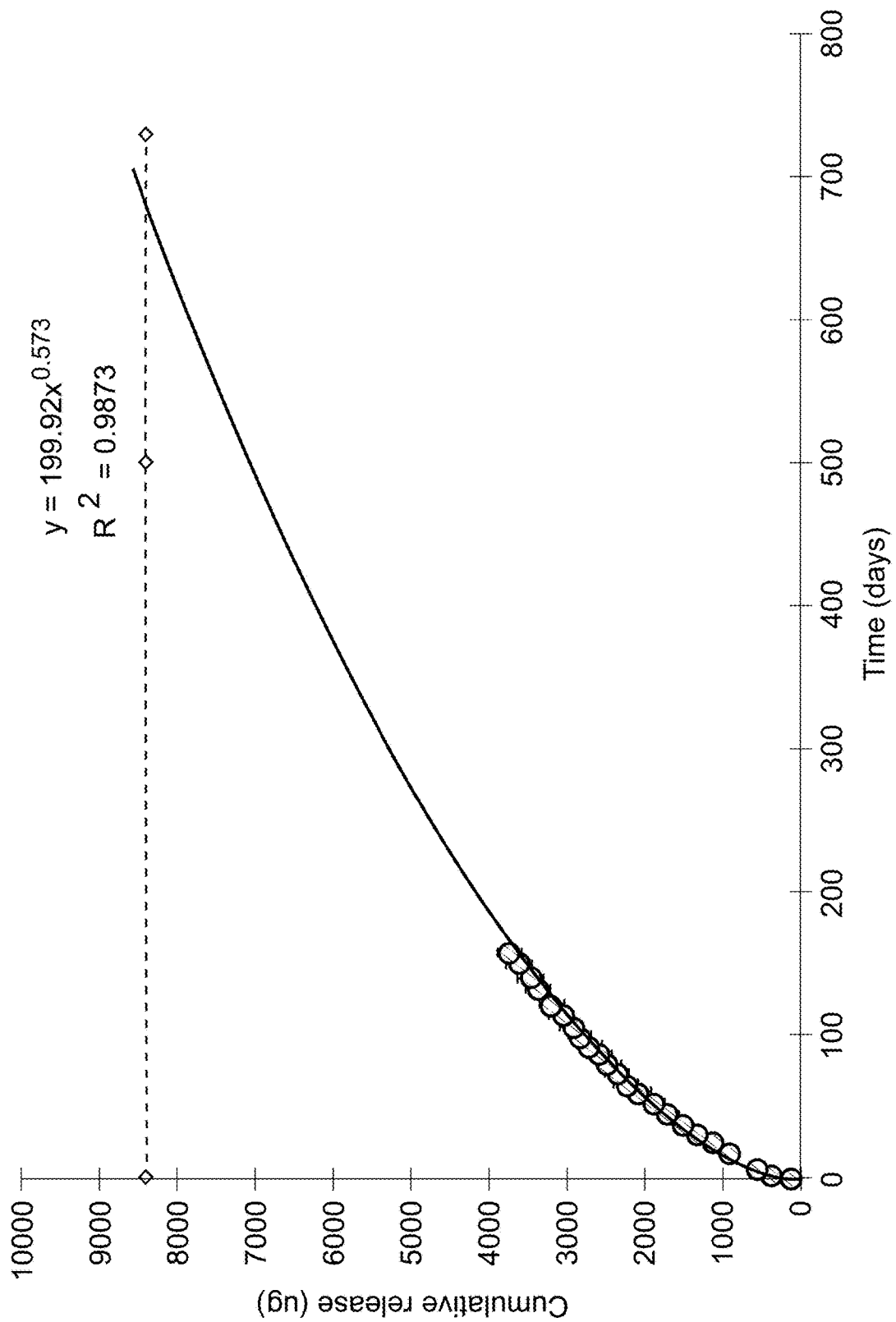
FIG. 4F depicts a predicted cumulative release profile of an implant containing 60% w/w bicalutamide in an in vitro model.

FIG. 4D depicts the cumulative release (μg/day) of bicalutamide from an implant containing 60% w/w bicalutamide in an in vitro model. FIG. 4E depicts the release rate profile of bicalutamide from an implant containing 60% w/w bicalutamide in an in vitro model. FIG. 4F depicts a predicted cumulative release (ug/day) profile of an implant containing 60% w/w bicalutamide demonstrating that there is enough bicalutamide loaded within the implant to provide a therapeutically effective dose of drug for 2 years. The dotted line indicates the total amount of drug loaded in the implant (~8.4 mg).

Figure 4G:
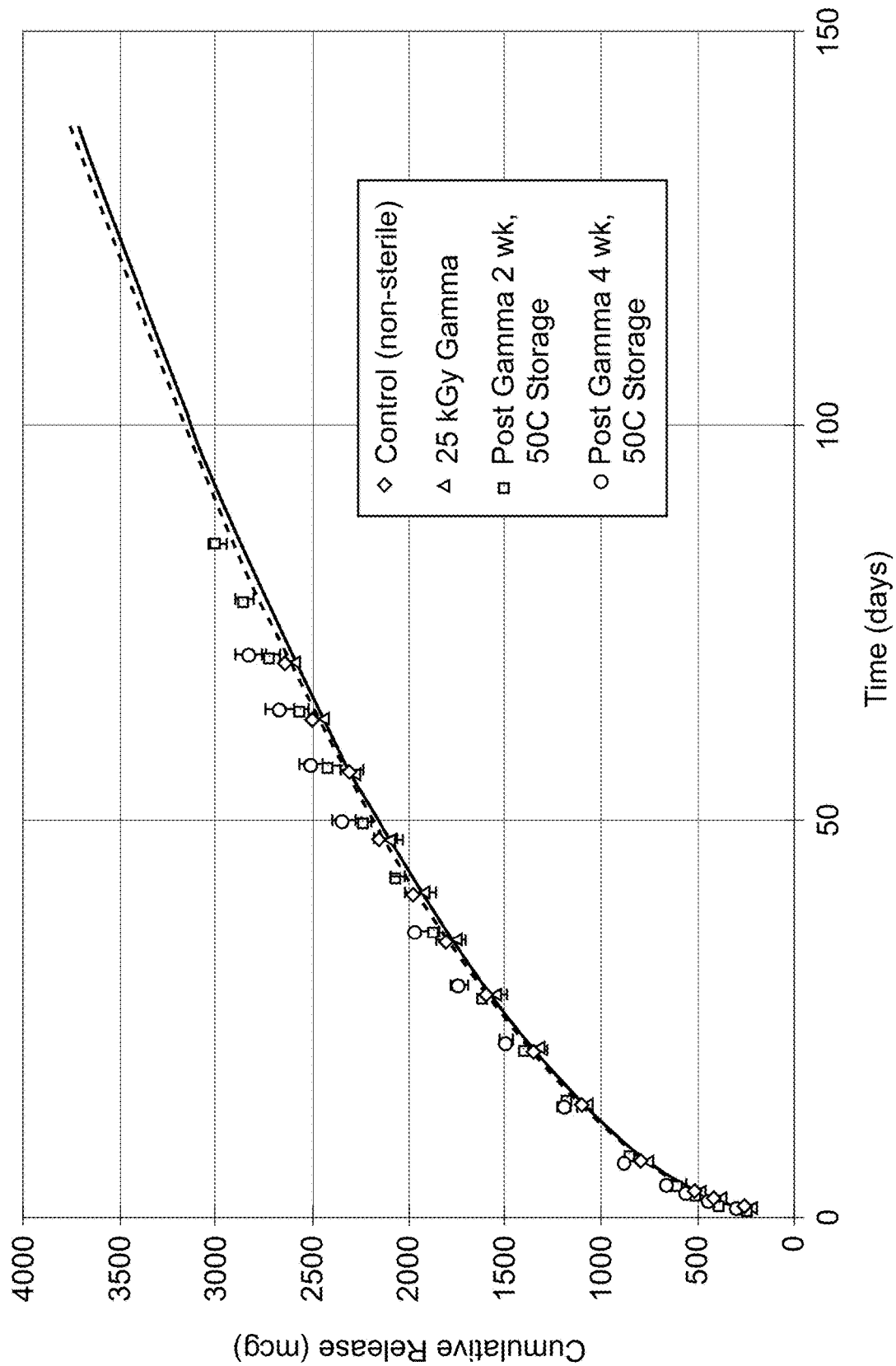
FIG. 4G depicts cumulative release profiles of implants containing 60% w/w bicalutamide in an in vitro model.
Figure 4H:
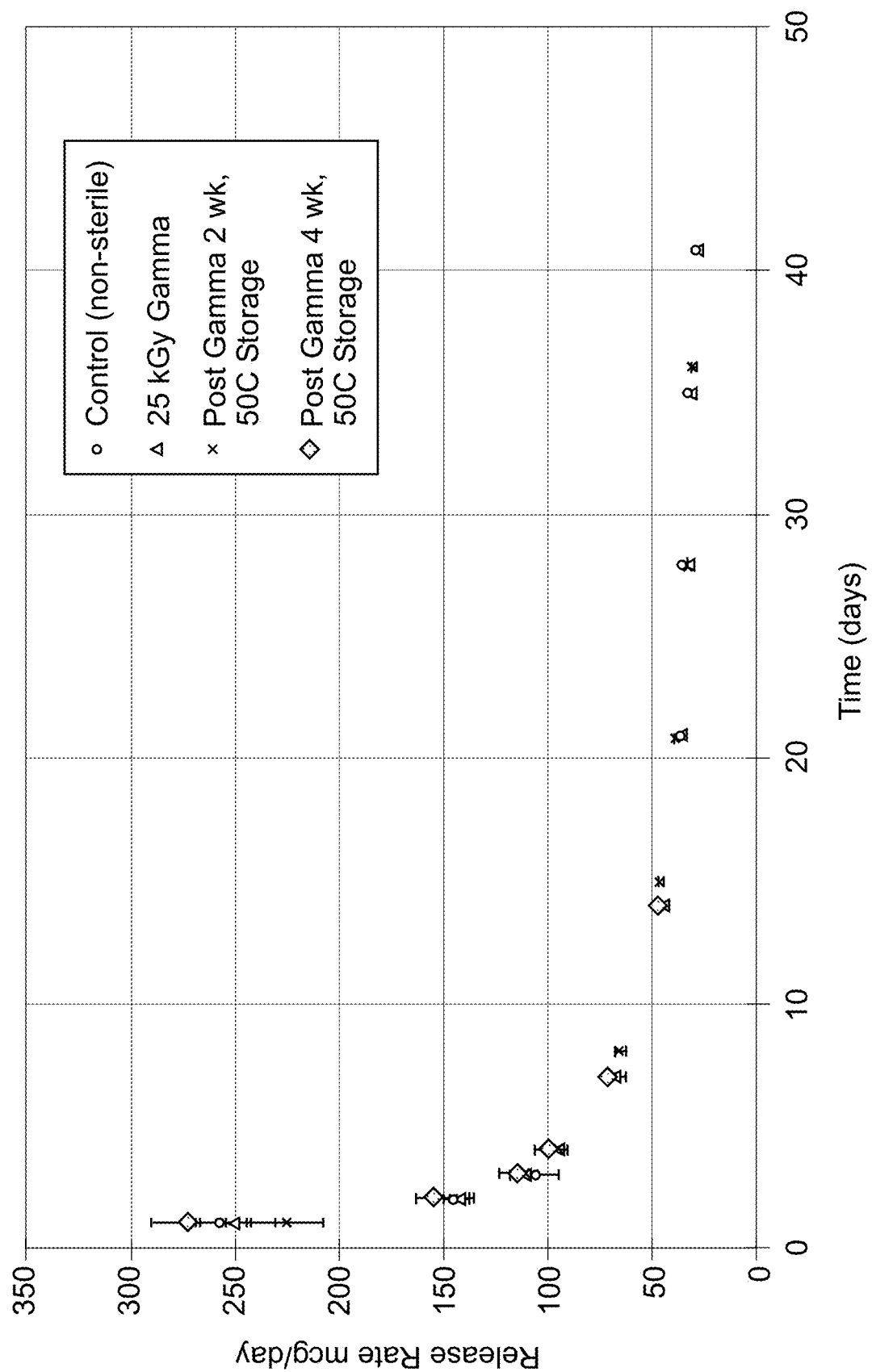
FIG. 4H depicts release rate profiles of implants containing 60% w/w bicalutamide in an in vitro model.

FIG. 4G depicts the impact of age, storage conditions, and sterilization on the cumulative release profiles of implants containing 60% w/w bicalutamide in an in vitro model. FIG. 4G demonstrates that different storage conditions, sterilization techniques, and age of the implants has no impact on the cumulative release profiles of these implants in an in vitro model. FIG. 4H depicts the release rate of bicalutamide from these implants, again demonstrating no effect from different storage conditions, sterilization techniques, or age of the implants in an in vitro model.

Simulated In Vivo Stability Assay

Figure 5:
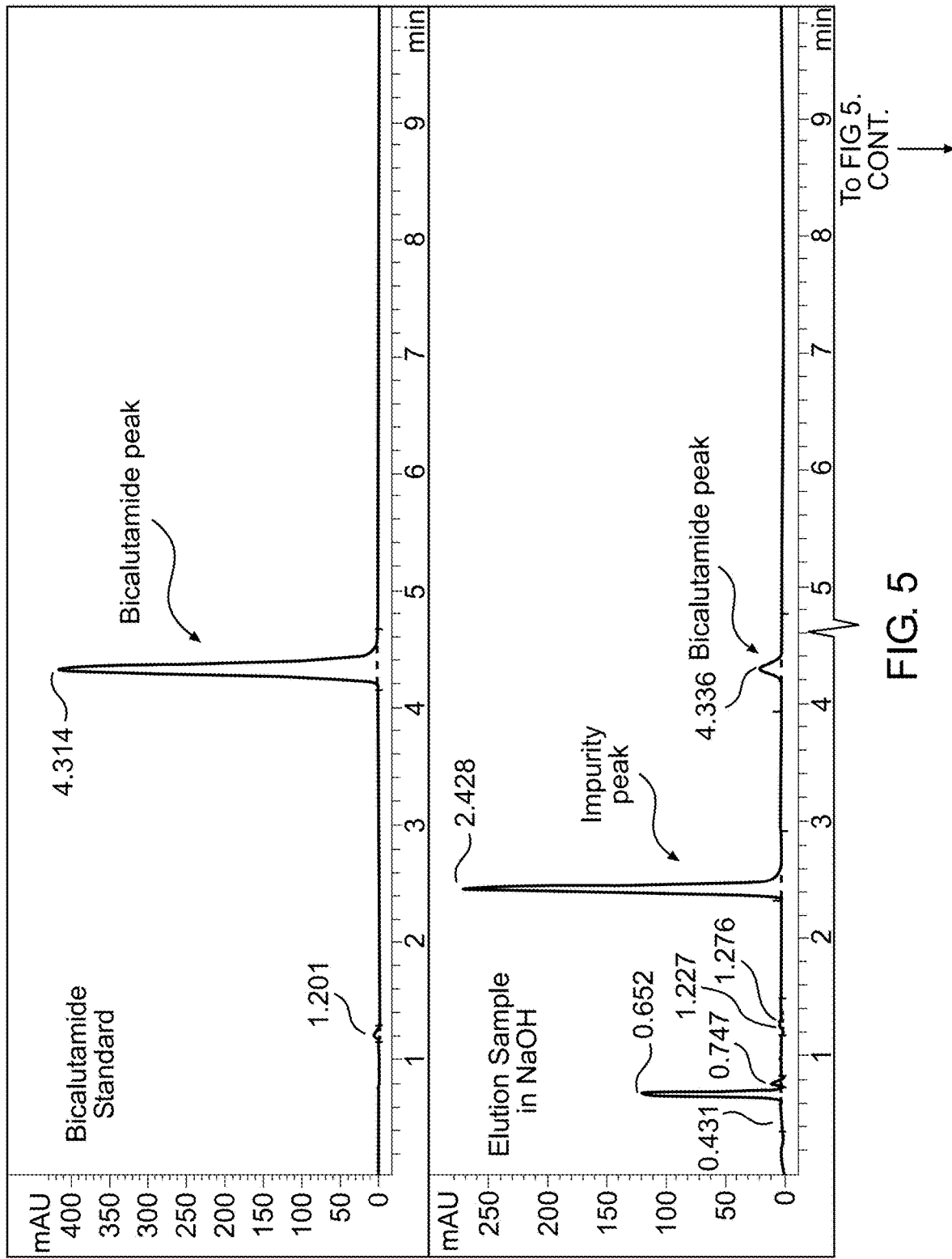
FIG. 5 depicts a non-limiting example of results obtained from a simulated in vivo stability assay.
Figure 5:
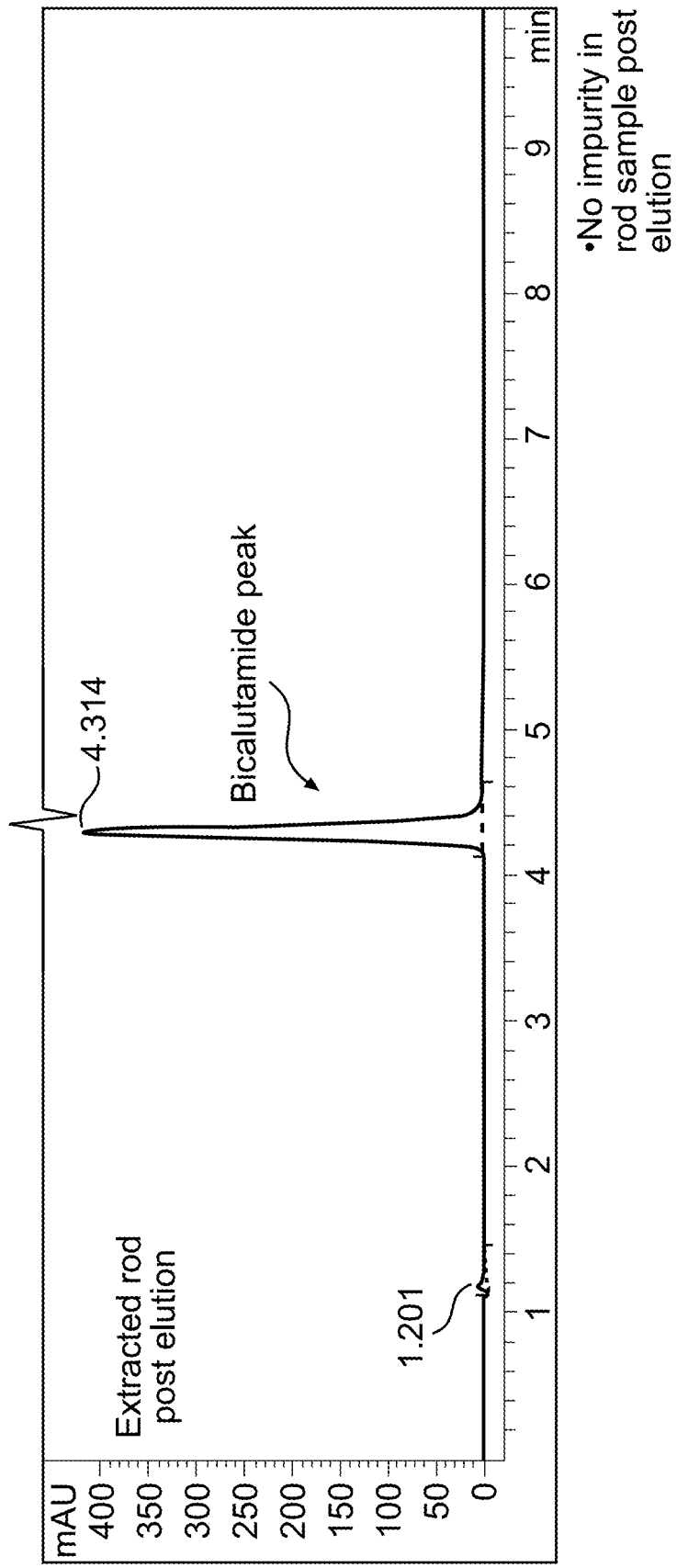

Simulated in vivo stability was performed to analyze the in vivo stability of active agent within the implant. Implants containing 0% w/w, 30% w/w, 45% w/w, and 60% w/w bicalutamide were placed in a 1% SDS solution containing 0.05 N NaOH (a degradant known to degrade bicalutamide) for ~8 hours at 37° C. Experimental controls included 0% w/w, 30% w/w, 45% w/w, and 60% w/w bicalutamide implants in 1% SDS without NaOH, as well as bicalutamide solution in 1% SDS with and without NaOH. Elution media and extracted bicalutamide from the implants were analyzed using reversed phase high-pressure liquid chromatography (RP-HPLC). Results demonstrated that bicalutamide eluent in all samples containing NaOH, including bicalutamide solution, exhibited degradation (25% to 40% by area) (see FIG. 5). In contrast, no degradation peaks were observed for the extracted samples. Thus, the implant prevented NaOH to penetrate the device thereby protecting the bicalutamide within the implant from degradation.

Example 3. Analysis of a Drug Implant of the Disclosure Implanted into the Prostate of Canines In this study, three canines, at least fifteen months old, were employed. Each canine received two active implant devices containing 60% by weight of bicalutamide (~8.4 mg)/Silbione Biomedical LSR D370 silicone in a 15 mm long by 0.95 mm diameter rod. An 18-gauge brachytherapy needle (OD 1.27 mm) was used for device implantation.

Clinical observations and body weight were recorded. Blood was collect at frequent intervals for determination of plasma bicalutamide concentrations and for clinical chemistry evaluation. After 55 days of observation, animals were euthanized and gross necropsy conducted, implanted devices were retrieved, and tissues (including prostate) were collected for histopathological examination and bicalutamide quantitation.

Live Animal Component

During surgical implantation, a single device was placed into each lobe of the prostate without complication. Placement of devices was confirmed by transrectal ultrasound during implantation and 1, 7, 14, and 28 days post-implantation. Mild to moderate swelling around the surgical incision site was observed in all three study animals, which was resolved with anti-inflammatory (carprofen) treatment. Blood was collected for clinical chemistry evaluation and bicalutamide quantitation. During the 55 days of observation, study animals exhibited no signs of distress or adverse effects from the test devices.

Gross Necropsy and Histopathology Interpretation 55 days post-implantation, study animals were euthanized and underwent gross necropsy. No test device related pathology was noted during necropsy. Organs were sampled for histopathological evaluation and bicalutamide quantitation. Prostate glands were trimmed and cut in three section perpendicular to the urethra: a cranial (rostral) section, a 3-5 mm transverse section, and a caudal section. From the rostral piece, two 5 mm punch biopsies were obtained surrounding the implant and the rest of the rostral and caudal section were divided in 4 sections each and sent for bicalutamide quantitation. The transverse piece in its entirety was sent for histopathological evaluation.

Histopathological evaluation found no device associated lesions in non-prostate tissues. Minimal kidney mineralization was observed but considered consistent with background findings in study canines. Prostates, testes, and epididymis were found to be mature and exhibited no device-related pathology. Device tracts were not visible, nor was any fibrotic encapsulation. Mild intergland fibrosis and lymphocytic infiltration was observed in some animals but deemed consistent with purpose-bred study canines.

Plasma Drug Quantification

Figure 6A:
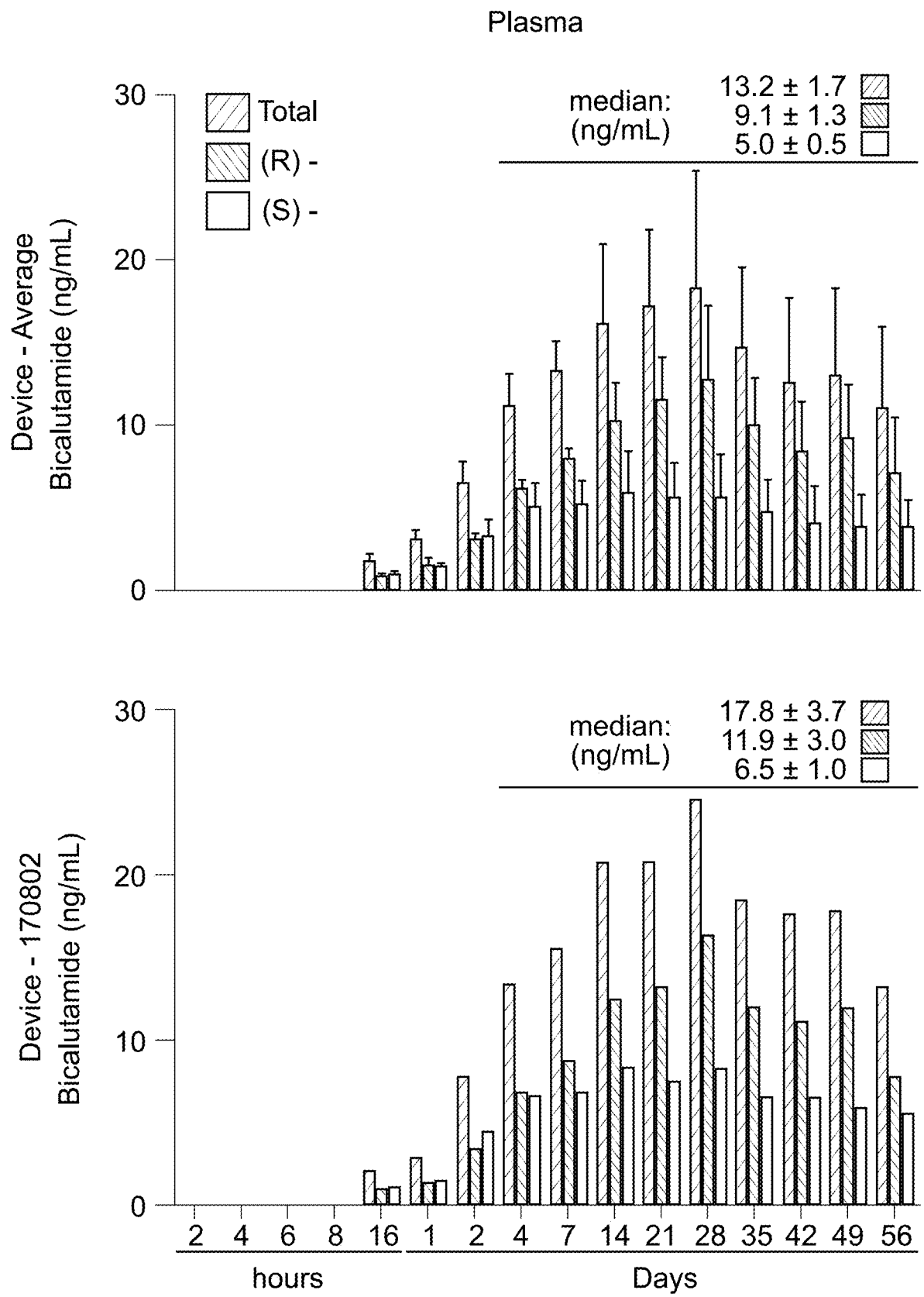
FIG. 6A and FIG. 6B depict non-limiting examples of bicalutamide levels in plasma after implantation of devices of the disclosure into the prostate of canines.
Figure 6B:
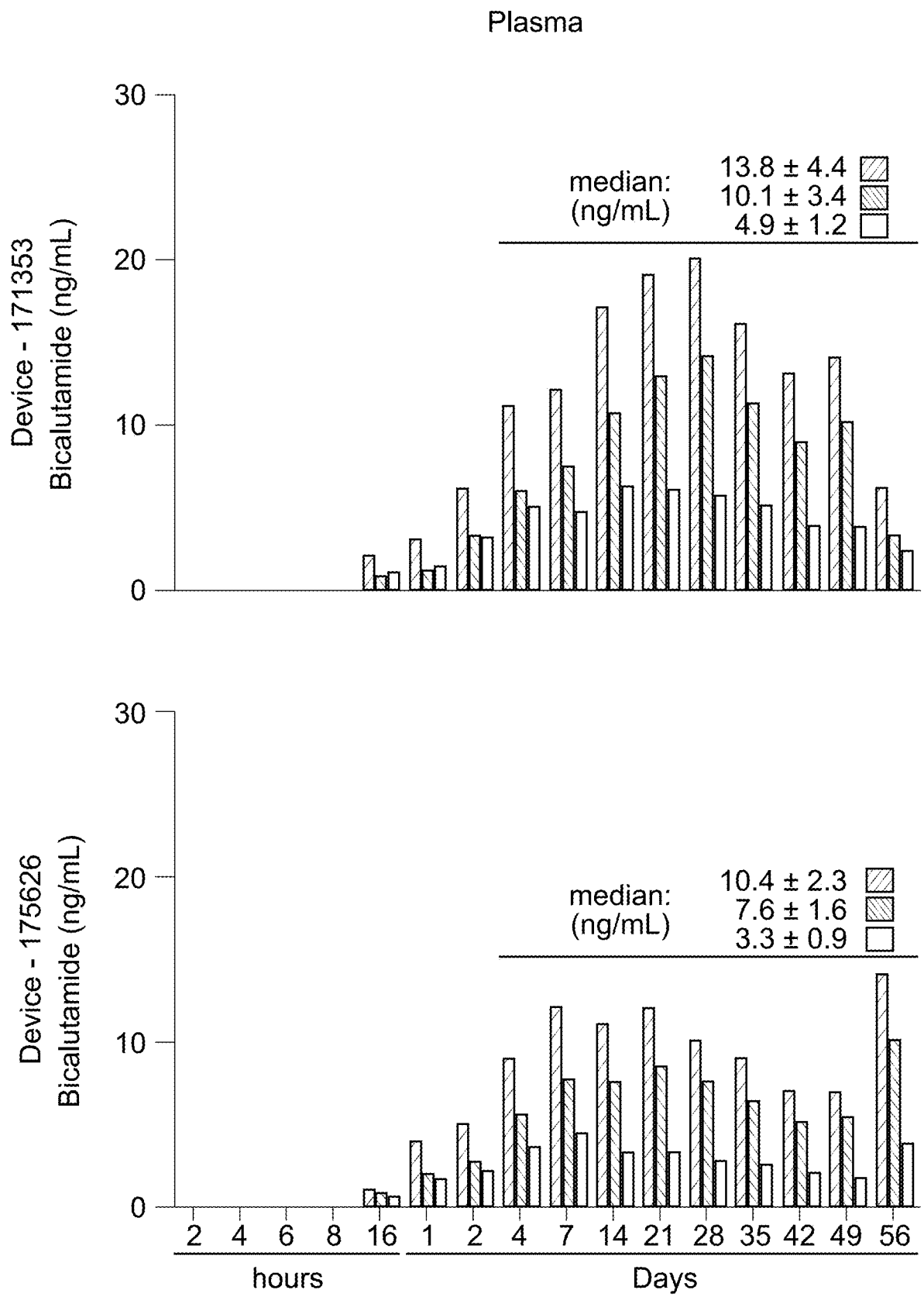

Plasma total, R-, and S-bicalutamide levels were comparable across all three study animals, peaking between 12 and 24 ng/mL (FIGS. 6A and 6B). Steady state was reached roughly by day 4 with average median levels of 13.2±1.7, 9.1±1.3, and 5.0±0.5 through day 55 for total, R-, and S-bicalutamide, respectively. The ratio of R- to S-bicalutamide was roughly 2:1. Note that the plasma levels as shown in FIGS. 6A and 6B are in micrograms for the oral dose while the scale is in ng/mL for the device plasma levels.

Solid Tissue Drug Quantification

Bicalutamide was quantified in major organs and prostate associated tissues harvested during necropsy. Bicalutamide levels were highest in organs of elimination (liver and kidney), as well as tested and lung. Consistent with plasma findings, the ratio of R- to S-bicalutamide was ~2:1. Compared to plasma levels, average accumulation was only apparent in liver (47±16, 28±9, and 19±7 ng/g versus 13±2, 9±1, and 5±1 ng/g, for total, R- and S-bicalutamide, respectively) but was very low compared to prostate exposure.

Prostate Gland Drug Quantification

Figure 7A:
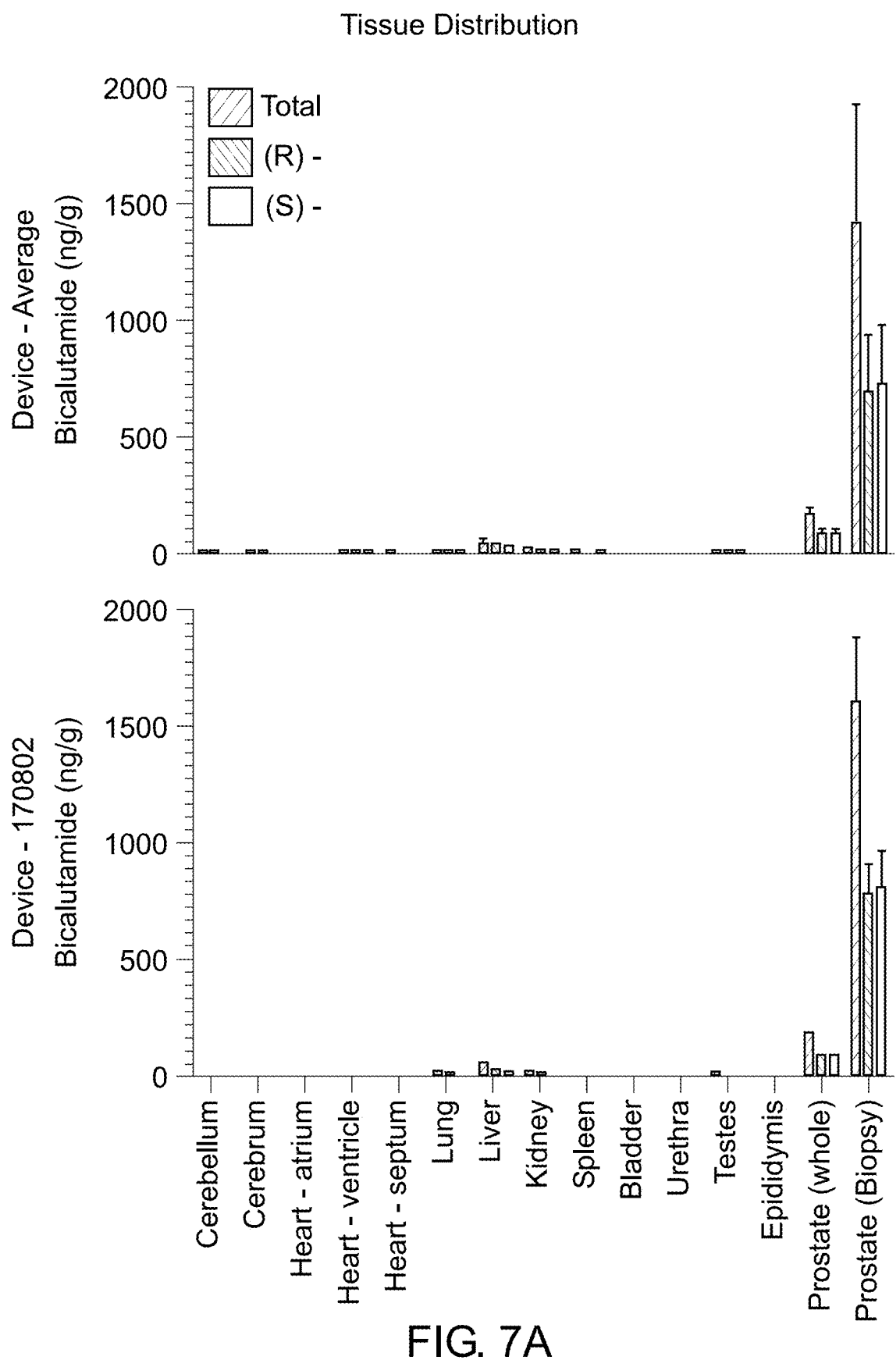
FIG. 7A and FIG. 7B depict non-limiting examples of bicalutamide levels in tissue after implantation of devices of the disclosure into the prostate of canines.
Figure 7B:
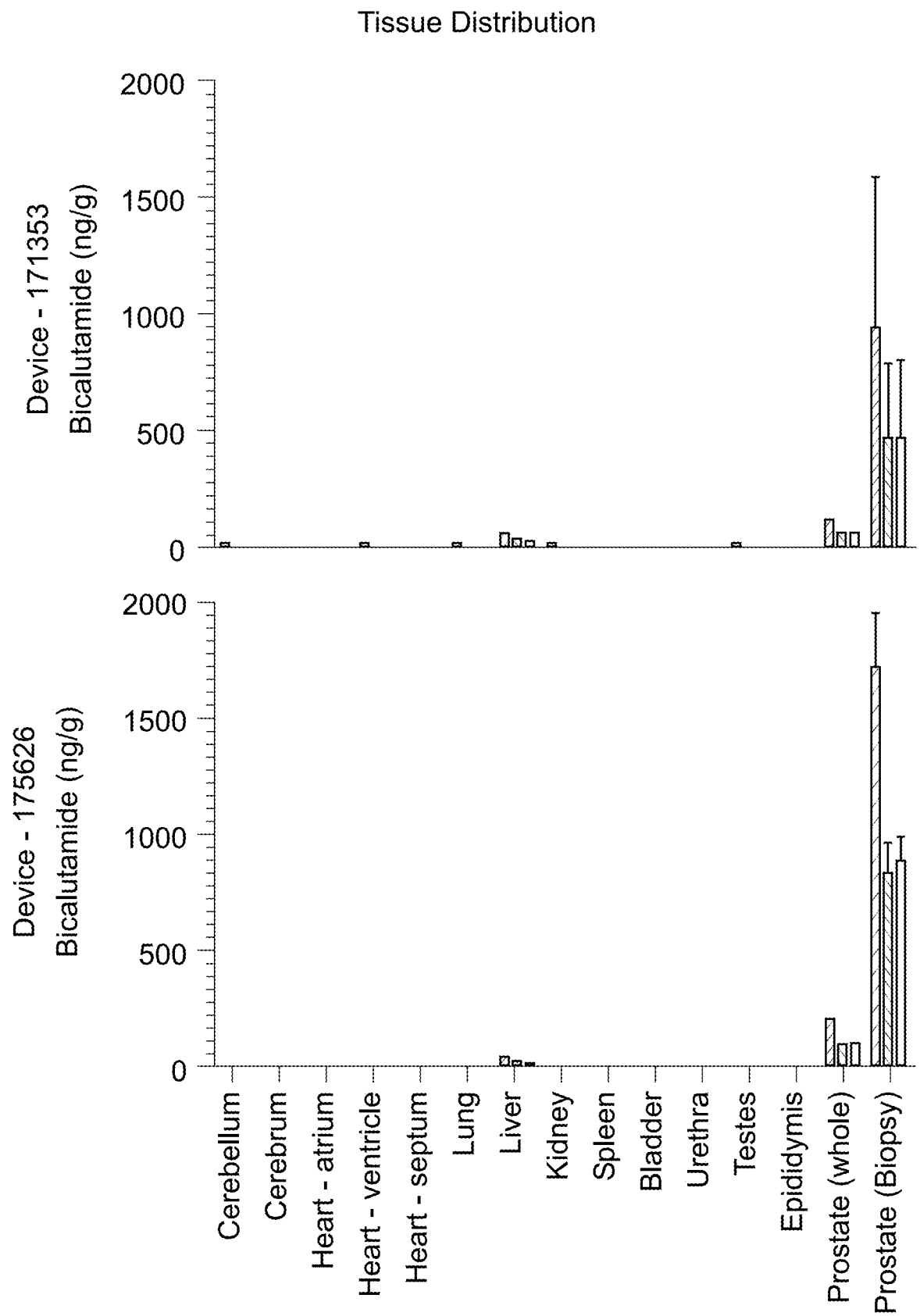
Figure 8:
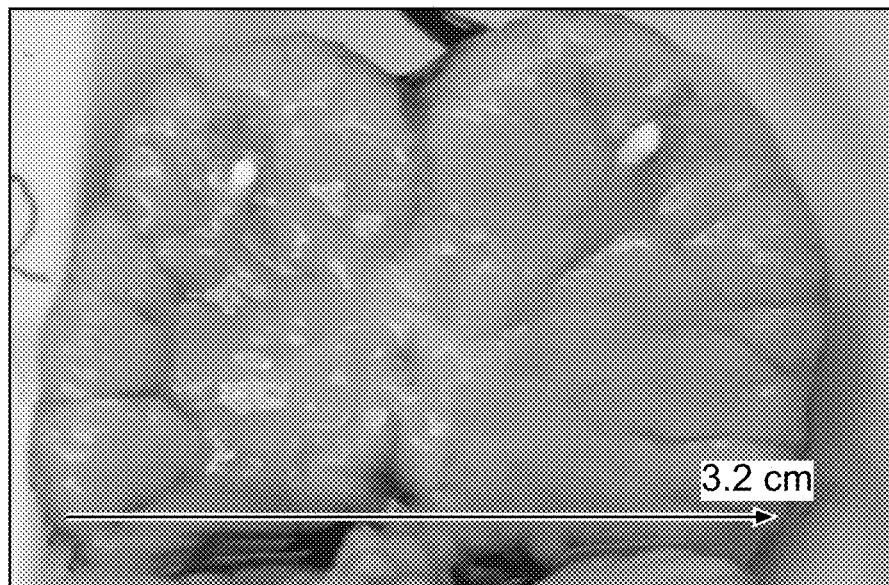
FIG. 8 depicts an image and a schematic of implant locations and local distribution of R-bicalutamide (active levels) in the rostral portion of the prostate of canines.
Figure 8:
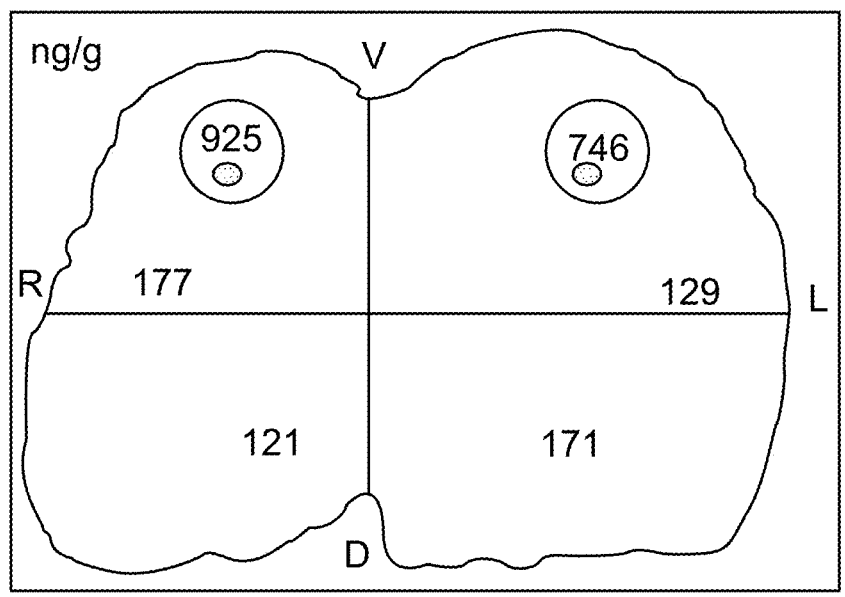

Quantitation of prostate bicalutamide found whole gland levels of total, R-, and S-bicalutamide to be 172±21, 86±10, and 87±11 ng/g, respectively. Punch biopsies 5 mm in diameter surrounding device implants resulted in an average total, R-, and S-bicalutamide of 1426±501, 698±242, and 727±259 ng/g, respectively (FIGS. 7A and 7B). Unlike plasma and other organs, the ratio of R- and S-bicalutamide in prostate was roughly 1:1. As seen in FIG. 8, the R-bicalutamide levels were higher surrounding the implant (red numbers in circles) with averages per quadrant (black numbers) demonstrating elution throughout the prostate.

Study Summary

The study sought to evaluate safety, toxicity, and bicalutamide tissue distribution in canines when two 60% bicalutamide by weight devices were implanted into the prostate. No significant safety or toxicity findings were observed during the live animal portion of the study. Consistently, gross and histopathological analysis of major organs and prostate-associated tissues found no lesions contributable to the study devices, including foreign body response, which might impair bicalutamide delivery to the prostate. Comparison of bicalutamide levels in plasma, organs, and prostate demonstrated significantly greater local (e.g., prostate) exposure was achieved. Whole prostate gland levels achieved for the active R-bicalutamide isomer (84.6±10.1 ng/g or 196.6±23.5 nM) is sufficient to inhibit the androgen receptor in cell-free androgen binding studies ($IC_{50}$-190 nM). Prostate tissue within ~5 mm of the device reached R-bicalutamide levels (698±242 ng/g or 1623±562 nM) demonstrated to inhibit prostate cancer cells ($IC_{50}$-1000 nM). The even distribution of R- and S-bicalutamide (~1:1) found in the prostate supports device delivery, rather than systemic recirculation, as isomeric formulation in the device is ~1:1, while hepatic metabolism results in a systemic ratio of 2:1 in this canine model.

The prostate was divided into three pieces to enable a more thorough assessment of bicalutamide delivery, while preserving the ability to evaluate histopathology. Although limited to a relatively thin transverse section of the prostate, this centrally positioned slice would be in contact or in close proximity to implanted devices and thus enable histopathological analysis of device and delivered bicalutamide impact on tissue. Further, having sent the center transverse section of the prostate for histopathology, its contribution to whole gland prostate bicalutamide level was not included. This likely results in an underestimation of whole gland bicalutamide as this device proximal portion likely had higher average levels than other portions of the gland (e.g., caudal piece), which were more distant from devices.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A drug/polymer composite prostate implant comprising: a silicone rubber matrix having a Shore A hardness of at least 30 durometer; and bicalutamide in solid form having a D90 of less than 15 microns dispersed in the silicone rubber matrix at an amount of at least 30% w/w of the total implant, wherein the prostate implant releases between 0.6 µg/day and 10 µg/day of the bicalutamide at 2-years after implantation in a subject.

2. The prostate implant of claim 1, wherein the solid form has a median particle size of less than 10 microns.

3. The prostate implant of claim 1, wherein the silicone has a curing temperature less than a melting point of bicalutamide.

4. The prostate implant of claim 1, wherein at least 50% of the bicalutamide remains in the silicone rubber matrix after 100 days of implantation.

5. The prostate implant of claim 1, wherein the silicone rubber matrix is a liquid silicone rubber.

6. The prostate implant of claim 1, wherein a volume of the prostate implant is at least 10 mm$^3$.

7. The prostate implant of claim 1, wherein a length of the prostate implant is from 1 mm to 30 mm.

8. The prostate implant of claim 1, wherein a length of the prostate implant is from 5 mm to 25 mm.

9. The prostate implant of claim 1, wherein a diameter of the prostate implant is from 0.1 mm to 1.5 mm.

10. The prostate implant of claim 1, wherein the bicalutamide is dispersed in the silicone rubber matrix at an amount of at least 40% w/w of the total implant.

11. The prostate implant of claim 1, wherein at least 50% of an outer surface of the silicone rubber matrix is uncoated.

12. The prostate implant of claim 1, wherein the prostate implant is deliverable using a canula of a needle.

13. The prostate implant of claim 1, consisting essentially of the silicone rubber matrix and the bicalutamide dispersed in the silicone rubber matrix.

14. The prostate implant of claim 1, wherein the bicalutamide is in crystalline form.

15. The prostate implant of claim 1, wherein the bicalutamide is in solid, amorphous form.

16. The prostate implant of claim 1, wherein the outer surface of the prostate implant silicone rubber matrix is coated.

* * * * *